United States Patent
Caiazza et al.

(10) Patent No.: US 10,584,347 B2
(45) Date of Patent: Mar. 10, 2020

(54) PRODUCTION OF PROTEINS IN LABYRINTHULOMYCETES

(71) Applicant: Conagen Inc., Bedford, MA (US)

(72) Inventors: Nicky C. Caiazza, Rancho Santa Fe, CA (US); Jun Urano, Irvine, CA (US); Maung N. Win, San Diego, CA (US); Kent S. Boles, La Jolla, CA (US)

(73) Assignee: Conagen Inc., Bedford, MA (US)

( * ) Notice: Subject to any disclaimer, the term of this patent is extended or adjusted under 35 U.S.C. 154(b) by 246 days.

(21) Appl. No.: 15/460,038

(22) Filed: Mar. 15, 2017

(65) Prior Publication Data

US 2017/0268015 A1 Sep. 21, 2017

Related U.S. Application Data

(60) Provisional application No. 62/309,402, filed on Mar. 16, 2016.

(51) Int. Cl.
| | |
|---|---|
| *C12N 15/68* | (2006.01) |
| *C12N 15/82* | (2006.01) |
| *C07K 16/28* | (2006.01) |
| *C07K 16/00* | (2006.01) |
| *C07K 16/24* | (2006.01) |
| *C12N 15/80* | (2006.01) |
| *C07K 14/405* | (2006.01) |
| *C07K 16/30* | (2006.01) |
| *C07K 16/32* | (2006.01) |

(52) U.S. Cl.
CPC ........ *C12N 15/8258* (2013.01); *C07K 14/405* (2013.01); *C07K 16/00* (2013.01); *C07K 16/24* (2013.01); *C07K 16/241* (2013.01); *C07K 16/248* (2013.01); *C07K 16/249* (2013.01); *C07K 16/2803* (2013.01); *C07K 16/2809* (2013.01); *C07K 16/2839* (2013.01); *C07K 16/2866* (2013.01); *C07K 16/2875* (2013.01); *C07K 16/2878* (2013.01); *C07K 16/2896* (2013.01); *C07K 16/3069* (2013.01); *C07K 16/32* (2013.01); *C12N 15/80* (2013.01); *C07K 2317/14* (2013.01); *C07K 2317/21* (2013.01); *C07K 2317/24* (2013.01); *C07K 2317/31* (2013.01); *C07K 2317/51* (2013.01); *C07K 2317/515* (2013.01); *C07K 2317/622* (2013.01); *C07K 2317/732* (2013.01); *C07K 2317/76* (2013.01); *C07K 2319/036* (2013.01)

(58) Field of Classification Search
None
See application file for complete search history.

(56) References Cited

U.S. PATENT DOCUMENTS

| | | | |
|---|---|---|---|
| 7,001,772 B2 | 2/2006 | Roessler et al. | |
| 7,211,418 B2 | 5/2007 | Metz et al. | |
| 7,217,856 B2 | 5/2007 | Weaver et al. | |
| 7,635,472 B2 * | 12/2009 | Kufer ................. | C07K 16/2803 424/130.1 |
| 7,759,097 B2 | 7/2010 | Ono et al. | |
| 7,851,191 B2 | 12/2010 | Roessler et al. | |
| 7,888,123 B2 | 2/2011 | Ono et al. | |
| 8,003,772 B2 | 8/2011 | Weaver et al. | |
| 8,206,984 B2 | 6/2012 | Roessler et al. | |
| 8,697,359 B1 | 4/2014 | Zhang | |
| 8,883,993 B2 | 11/2014 | Schneider et al. | |
| 2004/0235127 A1 | 11/2004 | Metz | |
| 2006/0275904 A1 | 12/2006 | Ono et al. | |
| 2009/0093033 A1 | 4/2009 | Luy | |
| 2010/0034823 A1 | 2/2010 | Borhani et al. | |
| 2010/0178298 A1 | 7/2010 | Lindhofer | |
| 2010/0233760 A1 * | 9/2010 | Apt ......................... | C07K 14/37 435/69.1 |
| 2012/0322116 A1 | 12/2012 | Sakaguchi et al. | |
| 2013/0323780 A1 | 12/2013 | Schneider et al. | |
| 2015/0132803 A1 | 5/2015 | Apt et al. | |
| 2016/0177255 A1 | 6/2016 | Radakovits et al. | |
| 2018/0201941 A1 | 7/2018 | Caiazza et al. | |

FOREIGN PATENT DOCUMENTS

| | | |
|---|---|---|
| EP | 1414941 B1 | 10/2002 |
| EP | 2623588 A1 | 8/2013 |
| EP | 3265567 | 1/2018 |
| WO | WO 2006/014685 A1 | 2/2006 |

(Continued)

OTHER PUBLICATIONS

Yamanishi et al., A Genome-Wide Activity Assessment of Terminator Regions in *Saccharomyces cerevisiae* Provides a "Terminatome" Toolbox, ACS Synthetic Biology, vol. 2, pp. 337-347, 2013 (Year: 2013).*

Genbank, 1N8Z_A, Chain A, Herceptin Fab (antibody)—Light Chain, retrieved from:https://www.ncbi.nlm.nih.gov/protein/28948772?sat=16&satkey=10451034 (Year: 2012).*

International Search Report dated Jul. 7, 2017, regarding PCT/US2017/022539.

(Continued)

*Primary Examiner* — Mindy G Brown

(74) *Attorney, Agent, or Firm* — Wolf, Greenfield & Sacks, P.C.; Karen K. Chan

(57) ABSTRACT

The present invention provides recombinant host cells that produce proteins or therapeutic proteins, and nucleic acid constructs for producing the cells. The cells have nucleic acid constructs that encode a heterologous protein, for example an antibody. The nucleic acid constructs also can have a functional signal sequence that directs the secretion of the protein from the cell. The signal sequence can be any functional signal sequence, and various signal sequences are disclosed herein. The invention also provides methods of producing the proteins.

21 Claims, 13 Drawing Sheets

Specification includes a Sequence Listing.

(56) References Cited

FOREIGN PATENT DOCUMENTS

| WO | WO 2007/006570 A2 | 1/2007 |
|---|---|---|
| WO | WO 2007/084922 A2 | 7/2007 |
| WO | WO 2013/144257 A1 | 10/2013 |
| WO | WO 2012/120375 A2 | 9/2016 |

OTHER PUBLICATIONS

International Search Report and Written Opinion dated Jun. 20, 2016 for Application No. PCT/US2016/020114.
International Preliminary Report on Patentability dated Sep. 5, 2017 for Application No. PCT/US2016/020114.
International Search Report and Written Opinion dated Jul. 7, 2017 for Application No. PCT/US2017/022539.
International Preliminary Report on Patentability dated Sep. 18, 2018 for Application No. PCT/US2017/022539.
[No Author Listed], Approval of Humira II-adalimumab by EMEA, Jan. 1, 2004, XP055624077, Retrieved from the Internet: URL:https://www.ema.europa.eu/en/documents/scientific-discussion/humira-epar-scientific-discussion_en.pdf [retrieved on Sep. 19, 2019]. 25 pages.
[No Author Listed], Genbank AB557594.1, Expression vector beta-act-loxP-RFP-loxP-GFP DNA. 2010.
[No Author Listed], NCBI GenBank accession No. DQ356659.1. Feb. 24, 2009.
[No Author Listed], NCBI GenBank accession No. JX978726.1. Jan. 9, 2015.
[No Author Listed], NCBI GenBank accession No. KC218923.1. Apr. 30, 2013.
Altschul et al., Basic local alignment search tool. J Mol Biol. Oct. 5, 1990;215(3):403-10.
Bayne et al., Vaccination against influenza with recombinant hemagglutinin expressed by Schizochytrium sp. confers protective immunity. PLoS One. Apr. 23, 2013;8(4):e61790. doi: 10.1371/journal.pone.0061790. Print 2013.
Chung et al., Insertional inactivation studies of the csmA and csmC genes of the green sulfur bacterium Chlorobium vibrioforme 8327: the chlorosome protein CsmA is required for viability but CsmC is dispensable. FEMS Microbiol Lett. Jul. 15, 1998;164(2):353-61.
Ferrante et al., An optimized, chemically regulated gene expression system for Chlamydomonas. PLoS One. Sep. 12, 2008;3(9):e3200. doi: 10.1371/journal.pone.0003200.
Garcia-Vedrenne et al., Development of genomic resources for a thraustochytrid pathogen and investigation of temperature influences on gene expression. PLoS One. Sep. 17, 2013;8(9):e74196. doi: 10.1371/journal.pone.0074196.
Gerrish et al., Pancreatic beta cell-specific transcription of the pdx-1 gene. The role of conserved upstream control regions and their hepatic nuclear factor 3beta sites. J Biol Chem. Feb. 4, 2000;275(5):3485-92.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gibson, Enzymatic assembly of overlapping DNA fragments. Methods Enzymol. 2011;498:349-61. doi: 10.1016/B978-0-12-385120-8.00015-2.
Hellen et al., Internal ribosome entry sites in eukaryotic mRNA molecules. Genes Dev. Jul. 1, 2001;15(13):1593-612.
Henikoff et al., Amino acid substitution matrices from protein blocks. Proc Natl Acad Sci U S A. Nov. 15, 1992;89(22):10915-9.
Higo et al., Plant cis-acting regulatory DNA elements (PLACE) database: 1999. Nucleic Acids Res. Jan. 1, 1999;27(1):297-300.
Isett et al., Twenty-four-well plate miniature bioreactor high-throughput system: assessment for microbial cultivations. Biotechnol Bioeng. Dec. 1, 2007;98(5):1017-28.
Ji et al., Genome Sequence of Schizochytrium sp. CCTCC M209059, an Effective Producer of Docosahexaenoic Acid-Rich Lipids. Genome Announc. Aug. 6, 2015;3(4). pii: e00819-15. doi: 10.1128/genomeA.00819-15.
Karlin et al., Applications and statistics for multiple high-scoring segments in molecular sequences. Proc Natl Acad Sci U S A. Jun. 15, 1993;90(12):5873-7.
Kellerman et al., Analysis of the primary structure and promoter function of a pyruvate decarboxylase gene (PDC1) from Saccharomyces cerevisiae. Nucleic Acids Res. Nov. 25, 1986;14(22):8963-77.
Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.
Kindle et al., Stable nuclear transformation of Chlamydomonas using the Chlamydomonas gene for nitrate reductase. J Cell Biol. Dec. 1989;109(6 Pt 1):2589-601.
Kindle, High-frequency nuclear transformation of Chlamydomonas reinhardtii. Proc Natl Acad Sci U S A. Feb. 1990;87(3):1228-32.
Kobayashi et al., Increase of eicosapentaenoic acid in thraustochytrids through thraustochytrid ubiquitin promoter-driven expression of a fatty acid { delta }5 desaturase gene. Appl Environ Microbiol. Jun. 2011;77(11):3870-6. doi: 10.1128/AEM.02664-10. Epub Apr. 8, 2011.
Komar et al., Cellular IRES-mediated translation: the war of ITAFs in pathophysiological states. Cell Cycle. Jan. 15, 2011;10(2):229-40. Epub Jan. 15, 2011.
Lescot et al., PlantCARE, a database of plant cis-acting regulatory elements and a portal to tools for in silico analysis of promoter sequences. Nucleic Acids Res. Jan. 1, 2002;30(1):325-7.
Lippmeier et al., Characterization of both polyunsaturated fatty acid biosynthetic pathways in Schizochytrium sp. Lipids. Jul. 2009;44(7):621-30. doi: 10.1007/s11745-009-3311-9. Epub Jun. 3, 2009.
Matsuda et al., Analysis of Δ-fatty acid desaturase function revealed that two distinct pathways are active for the synthesis of PUFAs in T. aureum ATCC 34304. J Lipid Res. Jun. 2012;53(6):1210-22. doi: 10.1194/jlr.M024935. Epub Feb. 26, 2012. Erratum in: J Lipid Res. Dec. 2012;53(12):2806.
McCarthy et al., Differential expression analysis of multifactor RNA-Seq experiments with respect to biological variation. Nucleic Acids Res. May 2012;40(10):4288-97. doi: 10.1093/nar/gks042. Epub Jan. 28, 2012.
Mendez-Alvarez et al., Transformation of Chlorobium limicola by a plasmid that confers the ability to utilize thiosulfate. J Bacteriol. Dec. 1994;176(23):7395-7. Erratum in: J Bacteriol Feb. 1995;177(4):1121.
Mogno et al., TATA is a modular component of synthetic promoters. Genome Res. Oct. 2010;20(10):1391-7. doi: 10.1101/gr.106732.110. Epub Jul. 13, 2010.
Mortazavi et al., Mapping and quantifying mammalian transcriptomes by RNA-Seq. Nat Methods. Jul. 2008;5(7):621-8. doi: 10.1038/nmeth.1226. Epub May 30, 2008.
Needleman et al., A general method applicable to the search for similarities in the amino acid sequence of two proteins. J Mol Biol. Mar. 1970;48(3):443-53.
Ohnuma et al., Polyethylene glycol (PEG)-mediated transient gene expression in a red alga, Cyanidioschyzon merolae 10D. Plant Cell Physiol. Jan. 2008;49(1):117-20. Epub Nov. 14, 2007.
Pasupathy et al., Direct plant gene delivery with a poly(amidoamine) dendrimer. Biotechnol J. Aug. 2008;3(8):1078-82. doi: 10.1002/biot.200800021.
Pearson et al., Improved tools for biological sequence comparison. Proc Natl Acad Sci U S A. Apr. 1988;85(8):2444-8.
Perrone et al., The Chlamydomonas IDA7 locus encodes a 140-kDa dynein intermediate chain required to assemble the I1 inner arm complex. Mol Biol Cell. Dec. 1998;9(12):3351-65.
Quinn et al., Copper response element and Crr1-dependent Ni(2+)-responsive promoter for induced, reversible gene expression in Chlamydomonas reinhardtii. Eukaryot Cell. Oct. 2003;2(5):995-1002.
Raghukumar, Thraustochytrid Marine Protists: production of PUFAs and Other Emerging Technologies. Mar Biotechnol (NY). Nov.-Dec. 2008;10(6):631-40. doi: 10.1007/s10126-008-9135-4. Epub Aug. 20, 2008.

(56) References Cited

OTHER PUBLICATIONS

Ranasinghe et al., An improved protocol for the isolation of total genomic DNA from Labyrinthulomycetes. Biotechnol Lett. Mar. 2015;37(3):685-90. doi: 10.1007/s10529-014-1712-1. Epub Oct. 30, 2014.
Rombauts et al., PlantCARE, a plant cis-acting regulatory element database. Nucleic Acids Res. Jan. 1, 1999;27(1):295-6.
Sakaguchi et al., Versatile transformation system that is applicable to both multiple transgene expression and gene targeting for Thraustochytrids. Appl Environ Microbiol. May 2012;78(9):3193-202. doi: 10.1128/AEM.07129-11. Epub Feb. 17, 2012.
Shagin et al., GFP-like proteins as ubiquitous metazoan superfamily: evolution of functional features and structural complexity. Mol Biol Evol. May 2004;21(5):841-50. Epub Feb. 12, 2004.
Shahmuradov et al., PlantProm: a database of plant promoter sequences. Nucleic Acids Res. Jan. 1, 2003;31(1):114-7.
Smith et al., Comparison of biosequences. Adv Appl Math. Dec. 1, 1981;2(4):482-9.
Trapnell et al., Differential gene and transcript expression analysis of RNA-seq experiments with TopHat and Cufflinks. Nat Protoc. Mar. 1, 2012;7(3):562-78. doi: 10.1038/nprot.2012.016. Erratum in: Nat Protoc. Oct. 2014;9(10):2513.
Watt et al., urg1: a uracil-regulatable promoter system for fission yeast with short induction and repression times. PLoS One. Jan. 16, 2008;3(1):e1428. doi: 10.1371/journal.pone.0001428.
Wolk et al., Construction of shuttle vectors capable of conjugative transfer from *Escherichia coli* to nitrogen-fixing filamentous cyanobacteria. Proc Natl Acad Sci U S A. Mar. 1984;81(5):1561-5.

\* cited by examiner

PRODUCTION OF PROTEINS IN LABYRINTHULOMYCETES

CROSS-REFERENCE TO RELATED APPLICATIONS

This application claims the benefit of U.S. provisional application Ser. No. 62/309,402, filed Mar. 16, 2016, which is hereby incorporated by reference in its entirety, including all Tables, Figures, and Claims.

INCORPORATION OF SEQUENCE LISTING

The material in the accompanying sequence listing is hereby incorporated by reference into this application. The accompanying sequence listing text file, name SGI2040_1_Sequence_Listing.txt, was created on Mar. 13, 2017, and is 47 kb. The file can be assessed using Microsoft Word on a computer that uses Windows OS.

FIELD OF THE INVENTION

The invention involves the production of proteins in Labyrinthulomycetes cells, methods of producing the proteins, and expression cassettes and other tools useful in the methods.

BACKGROUND OF THE INVENTION

Mammalian cell cultures are very useful for the production of certain products, such as viral vaccines, interferons, recombinant therapeutic proteins, and monoclonal antibodies. However, these cell cultures also carry inherent limitations, such as a very slow growth rate, low biomass density, the requirement for a complex media, and high operational costs.

Microbial expression systems have numerous advantages for the production of useful proteins. While certain microbial systems are useful for producing, simple proteins, such microbial systems would need to be improved in terms of the quality and complexity of proteins that can be produced. The improvement of microbial cell specific productivities requires complex engineering, and substantial understanding and rewiring of the underlying microbial metabolism. An ideal strain would be genetically stable, have a high specific and volumetric productivity, form no by-products, and use a well-defined medium. These characteristics would allow for downstream processing with a limited number of steps.

Labyrinthulomycetes are robustly fermentable eukaryotic microalgae. These heterotrophic microorganisms are recognized for their industrial ability to consume sugar and store large amounts of cellular oils as triglycerides; the most commercially important is docosahexaenoic acid (DHA), an omega-3 polyunsaturated fatty acid (PUFA) that is a major component of fish oil. These organisms produce oils that can be used in human and animal nutritional supplements, as well as for food fortification applications. These triglyceride oils can be produced in culture using inexpensive media. Because of these desirable qualities it would be advantageous to have recombinant Labyrinthulomycetes cells that are able to produce a variety of proteins or therapeutic proteins, including functional antibodies that can have both heavy and light chains.

SUMMARY OF THE INVENTION

The present invention provides recombinant Labyrinthulomycetes cells that produce proteins or therapeutic proteins, nucleic acid constructs such as expression cassettes for producing the cells, and methods of producing the cells and products of the cells. The cells have nucleic acid constructs that encode a heterologous protein, for example an antibody or other therapeutic protein. The nucleic acid constructs also can have a functional signal sequence that directs the secretion of the protein from the cell. The signal sequence can be any of various signal sequences disclosed herein, such as those nucleotide and amino acid sequences disclosed as SEQ ID NOs: 9-94.

In a first aspect the invention provides a recombinant Labyrinthulomycetes cell having an expression cassette that encodes a heterologous protein and a functional signal sequence that directs the secretion of the heterologous protein from the cell. The signal sequence can have at least 90% sequence identity to a sequence of at least 10 contiguous amino acids selected from any one of SEQ ID NO: 9-20 or 33-47 or 63-78, or can be encoded by a nucleic acid sequence having at least 90% sequence homology to SEQ ID NO: 21-32 or 48-62 or 79-94. In some embodiments the heterologous protein is a therapeutic protein, and can be a functional antibody, which can have at least one heavy chain and at least one light chain. The antibody can have an amino acid sequence selected from, but are not limited to, eculizumab, natalizumab, cetuximab, omalizumab, usteinumab, panitumumab, denosumab, trastuzumab and adalimumab.

In some embodiments the heterologous protein can be a bispecific T cell engager. The heterologous protein can have a binding molecule that binds to an antigen, for example anti-CD19, anti-CD3 anti-CD38, and prostate-specific membrane antigen (PSMA). Ile expression cassette can encode a promoter active in a Labyrinthulomycetes and that regulates transcription of the heterologous protein. The promoter can be, for example, tubulinα promoter (tubαp) or translation elongation factor (TEFp) promoter. The expression cassette can also encode a terminator, for example pgk1t or eno2t. When the heterologous protein is an antibody it can have a light chain and a heavy chain that have at least 90% sequence identity to an amino acid sequence of at least 100 contiguous amino acids of SEQ ID NO: 5 and 6 or SEQ ID NO: 7 and 8, respectively.

In another aspect the invention provides an expression cassette having at least one nucleotide sequence encoding a heterologous protein disclosed herein positioned to be regulated by the promoter, and at least one nucleotide sequence encoding a signal sequence having at least 80% or at least 85% or at least 90% sequence identity to a nucleotide sequence of at least 120 contiguous nucleotides selected from any one of SEQ ID NO: 21-32 or 48-62 or 79-94. The expression cassette can also have a promoter sequence and a terminator sequence functional in a Labyrinthulomycetes cell. In some embodiments the expression cassette is noncontiguous. The heterologous protein can be any antibody described herein, and can have a heavy chain and a light chain.

In another aspect the invention provides an antibody having a signal sequence functional in a Labyrinthulomycetes, a light chain having at least 90% sequence identity to SEQ ID NO: 5, and a heavy chain having at least 90% sequence identity to SEQ ID NO: 6; or a light chain having at least 90% sequence identity to SEQ ID NO: 7 and a heavy chain having at least 90% sequence identity to SEQ ID NO: 8. The signal sequence can be any described herein.

In another aspect the invention provides an *Aurantiochytrium* cell having an expression cassette that encodes an exogenous protein and a functional signal sequence that directs the secretion of the heterologous protein from the cell. The heterologous protein can be any described herein. The cell can produce at least 5 mg/L of the heterologous protein in a 24 hour period. The cell can have an expression cassette that encodes a promoter active in *Aurantiochytrium*; a terminator sequence active in *Aurantiochytrium*; the heterologous protein can be operably linked to the promoter; and a signal sequence having at least 90% sequence identity to at least 20 contiguous amino acids of a sequence selected from any one of SEQ ID NO: 9-20 or 23-47 or 63-78 or any signal sequence disclosed herein.

In another aspect the invention provides a method for producing any heterologous protein described herein. The method includes steps of cultivating a Labyrinthulomycetes cell that secretes a heterologous protein and that comprises an expression cassette encoding the heterologous protein and further encoding a functional signal sequence that directs the secretion of the heterologous protein from the cell; the signal sequence can have at least 90% sequence identity to a sequence of at least 20 contiguous amino acids selected from any one of SEQ ID NO: 9-20 or 33-47 or 63-78 or can be any described herein; and a step of harvesting the heterologous protein. The heterologous protein can be any described herein. The expression cassette can encode a promoter active in a Labyrinthulomycetes and that regulates transcription of the heterologous protein. The expression cassette can be any described herein, and the promoter and terminator can be any described herein. In one embodiment the promoter is tub-alpha-p or TEFp, and the terminator is pgk1t or eno2t.

In another embodiment the invention provides a therapeutic protein having an antibody molecule linked to a signal sequence. The therapeutic protein and the signal sequence can any described herein. In some embodiments the signal sequence is selected from SEQ ID NO: 9-20 or 33-47 or 63-78, and the antibody is anti-TNF-alpha or anti-HER2.

DETAILED DESCRIPTION OF THE DRAWINGS

FIG. 1 provides a schematic illustration of vectors and expression cassettes of the invention, identified as pCAB vectors with different expression cassettes (designated 018-030).

FIG. 2 is a general map of pCAB having homology arms and a unique BstZ17I site that is used to linearize these cassettes is also shown.

FIG. 3 is a bar graph showing the results of an HC-capture/LC-detect ELISA assay. Illustrated are the antibody titers of various clones. Clones 1-16 secrete anti-TNF-alpha antibody and clones 17-18 secrete anti-HER2 antibody.

Figure 6:
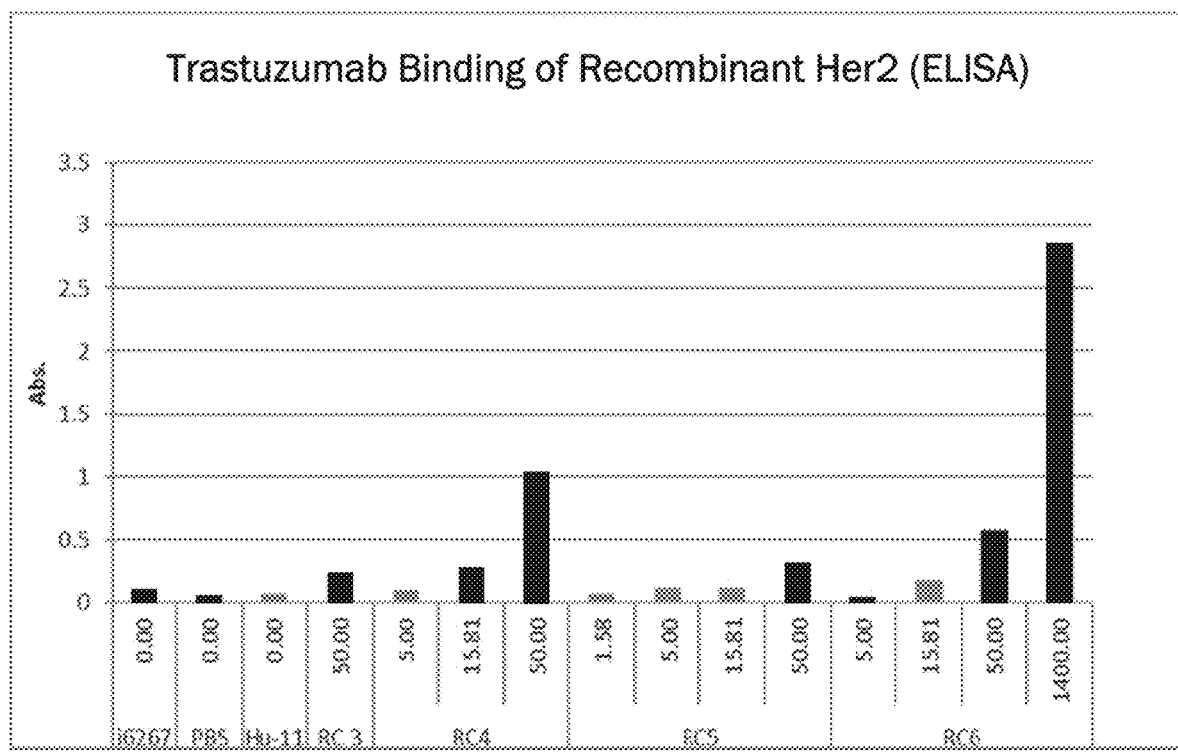

FIG. 6 is a bar graph showing the relative binding of anti-HER2 antibody to recombinant HER2. Binding is indicated by the amount of signal/absorbance (Abs.) detected by an ELISA assay. Titers used in the assay are displayed in mg/L above each antibody sample tested. i6267 is conditioned media; Hu-11 is anti-TNF-alpha supernatant (o/n culture); RC3 is protein A purified anti-TNF-alpha; RC4-RC6 are protein A purified anti-HER2.

Figure 7:
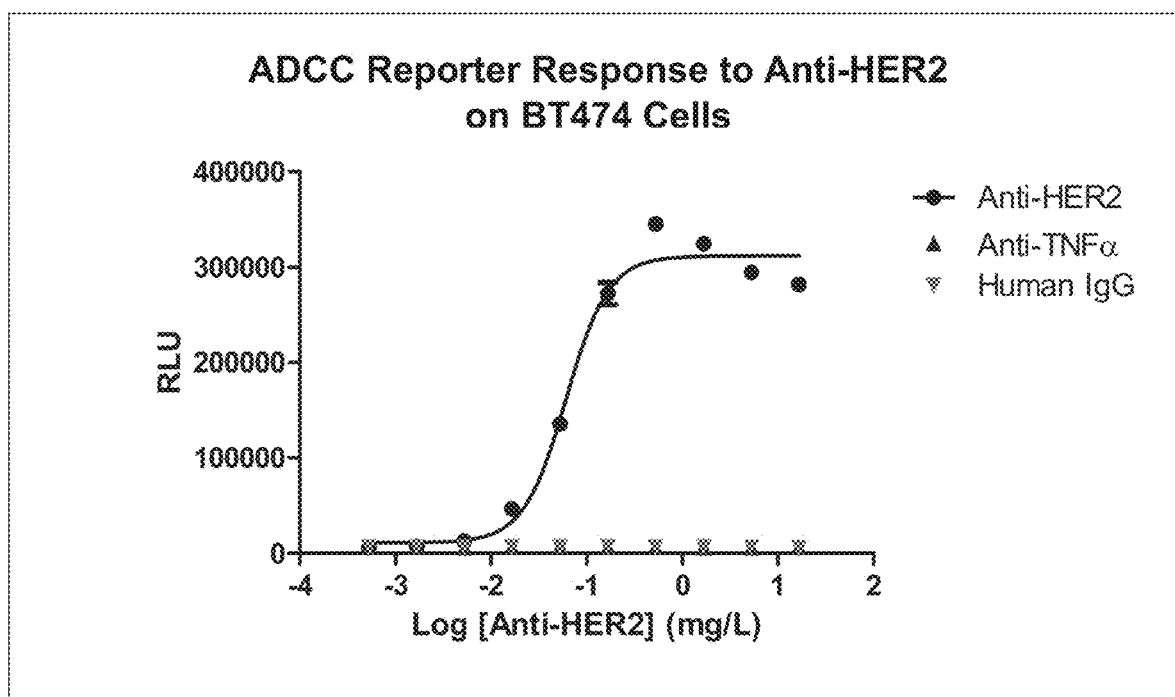

FIG. 7 provides a graph showing the antibody-dependent cell mediated cytotoxicity (ADCC) response to BT-474 cells targeted with purified anti-HER2.

Figure 8:
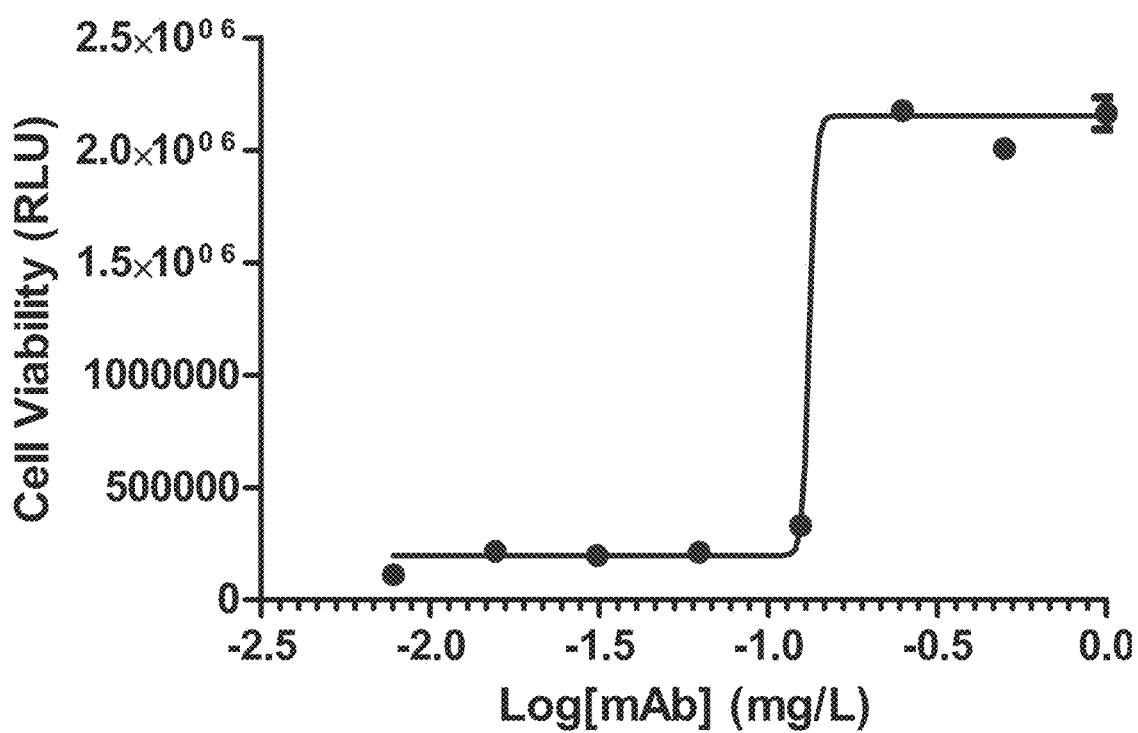

FIG. 8 provides a graph showing a concentration-dependent effect of anti-TNF-alpha on TNF-alpha-induced killing of L929 cells. The EC50 (g/ml) value is 1.3e-007.

Figure 9:
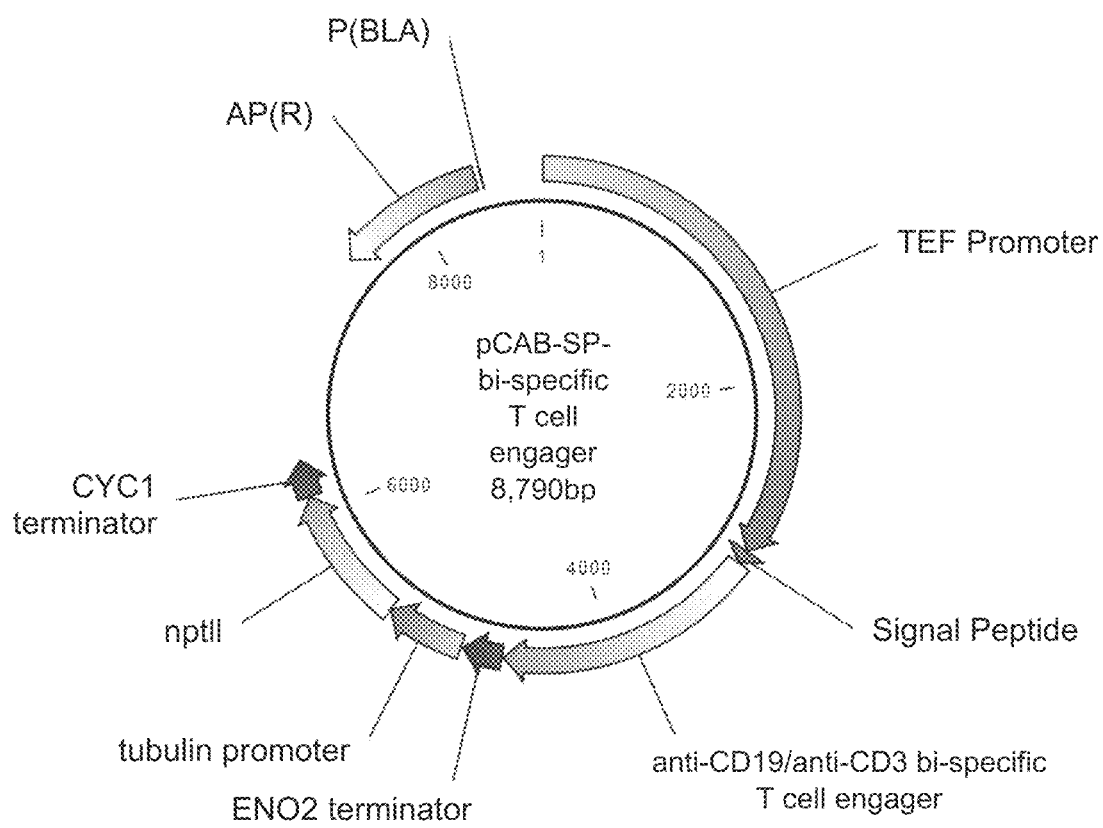

FIG. 9 provides a plasmid map for a construct used for the expression of anti-CD19/anti-CD3 bi-specific T cell engager Ab.

Figure 10A:
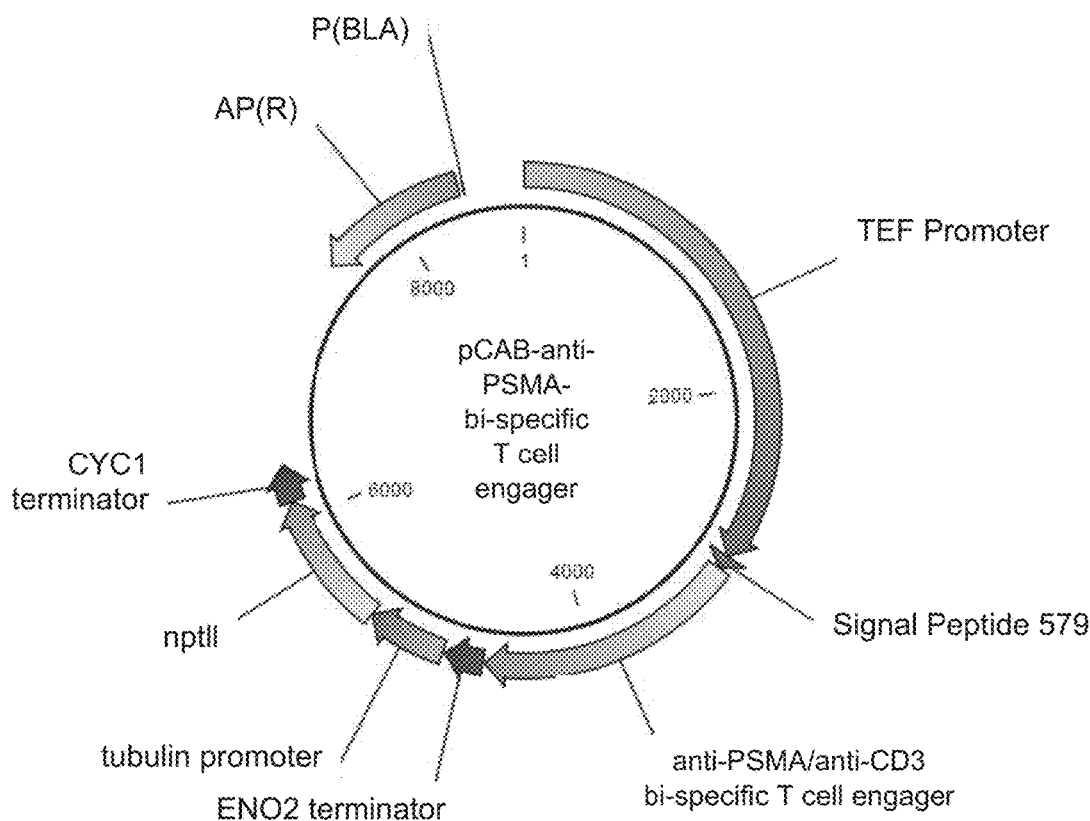
Figure 10B:
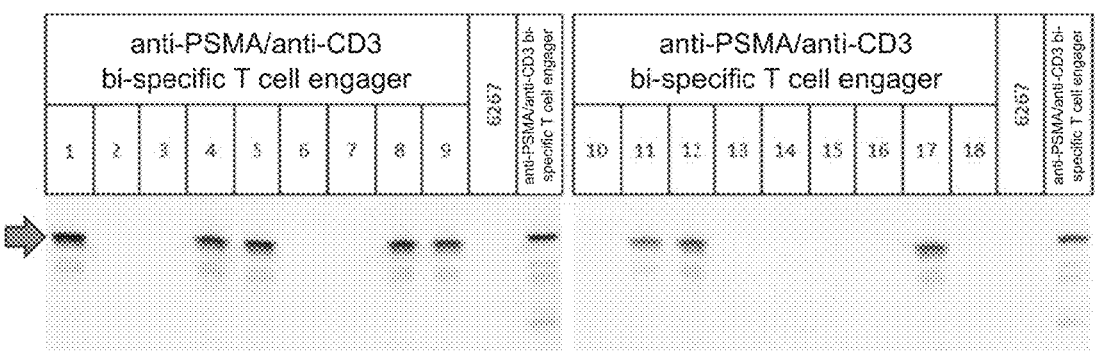

FIG. 10a provides a plasmid map for a construct used for expression of anti-PSMA/anti-CD3 bi-specific T cell engager antibody (PSMA-prostate-specific membrane antigen). FIG. 10b provides a Western blot indicating secretion of anti-PSMA/anti-CD3 bi-specific T cell engager antibody. The arrow indicates the expected size for the bi-specific T cell engager antibody.

Figure 11:
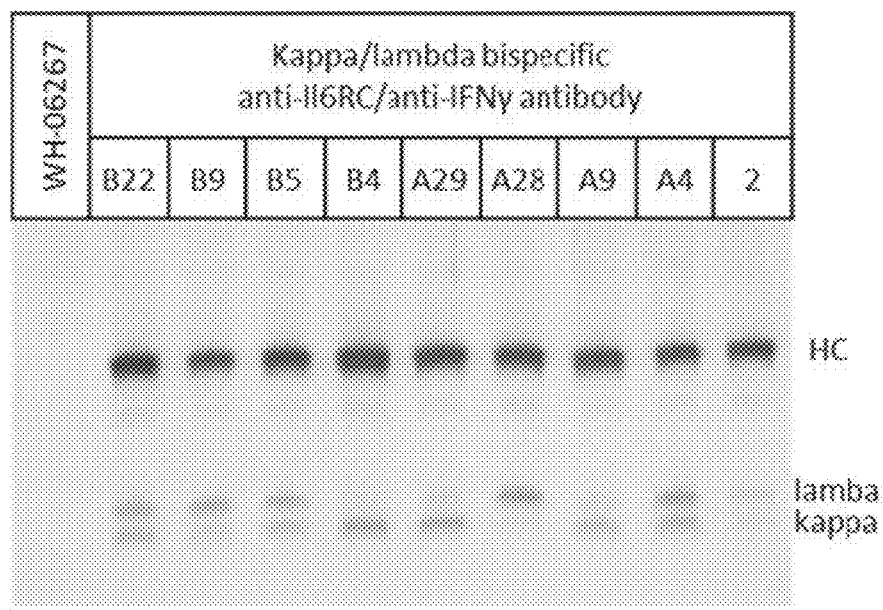

FIG. 11 provides a Western blot indicating secretion of the bispecific antibody anti-Il6RC/anti-IFNγ antibody. Bands corresponding to the heavy chain (HC), kappa light chain and lambda light chains are indicated.

Figure 12:
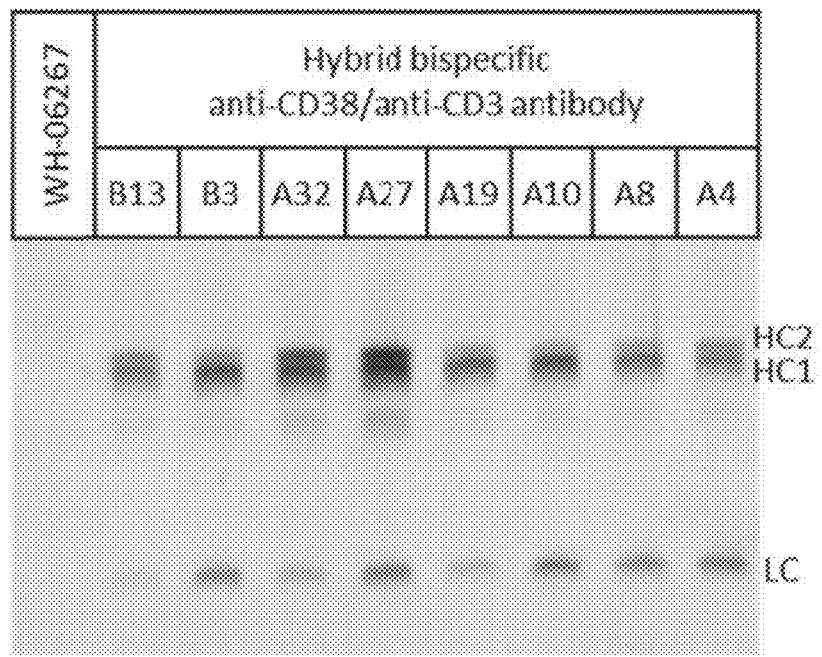

FIG. 12 provides a Western blot indicating secretion of the hybrid bispecific anti-CD38/anti-CD3 antibody (XENP13551). Bands corresponding to heavy chain 1 (HC1), heavy chain 2 (HC2), and light chain (LC) are indicated.

Figure 13:
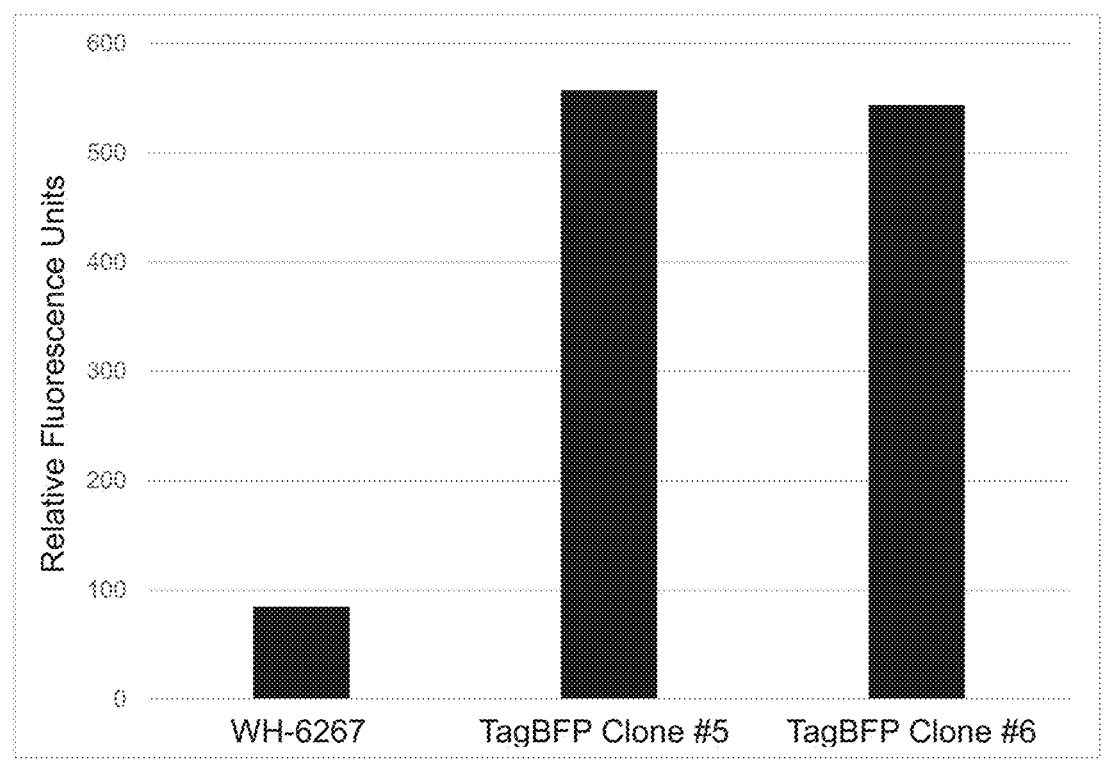

FIG. 13 is a graphical illustration of relative fluorescence in supernatant of cultures of strains expressing TagBFP. The background fluorescence from FM2 media was subtracted.

Figure 14:
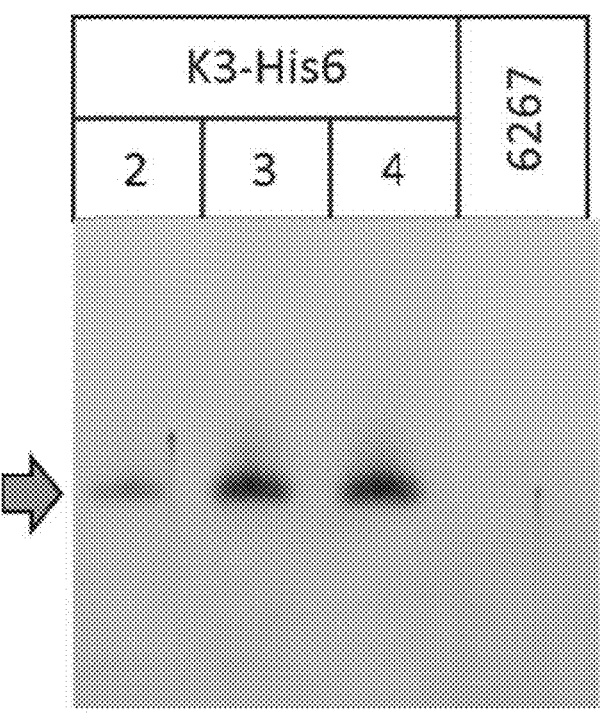

FIG. 14 provides a Western blot indicating secretion of K3-His6, indicated by the arrow.

DETAILED DESCRIPTION OF THE INVENTION

The recombinant cells, nucleic acid constructs, expression vectors, expression cassettes, and methods of the invention provide significant advantages over other tools and methods for producing proteins and other cell products. Labyrinthulomycetes cells have a very advantageous scalability that compares favorably to biomass titers achievable in yeast. Decreased fermentation cycle times carry the advantage of lower operational costs through lower material, energy, and labor costs per unit mass.

The cells of the invention offer a high fermentative capacity, which is desirable for cell-based production systems. The present invention leverages this advantage by providing methods for genetically manipulating the organisms to create a production platform for proteins or therapeutic proteins in one of the most highly productive, cost effective, and scalable fermentative eukaryotic microorganisms presently available.

In some embodiments the recombinant host cells or organisms of the invention can be any microorganism of the class Labyrinthulomycetes. While the classification of the Thraustochytrids and Labyrinthulids has evolved over the years, for the purposes of the present application, "labyrinthulomycetes" is a comprehensive term that includes microorganisms of the orders Thraustochytrid and Labyrinthulid, and includes (without limitation) the genera *Althornia, Aplanochytrium, Aurantiochytrium, Botyrochytrium, Corallochytrium, Diplophryids, Diplophrys, Elina, Japonochytrium, Labyrinthula, Labryinthuloides, Oblongichytrium, Pyrrhosorus, Schizochytrium, Thraustochytrium,* and *Ulkenia*. In some examples the microorganism is from a genus including, but not limited to, *Thraustochytrium, Labyrinthuloides, Japonochytrium,* and *Schizochytrium*. Alternatively, a host Labyrinthulomycetes microorganism can be from a genus including, but not limited to, *Aurantiochytrium, Oblongichytrium*, and *Ulkenia*. Examples of suitable microbial species within the genera include, but are not limited to: any *Schizochytrium* species, including, but not limited to, *Schizochytrium aggregatum, Schizochytrium limacinum, Schizochytrium minutum, Schizochytrium mangrovei, Schizochytrium marinum, Schizochytrium octosporum*, and any *Aurantiochytrium* species, any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any Japonochytrium species. Strains of Thraustochytriales that may be particularly suitable for the presently disclosed invention include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (ATCC 28209); *Schizochytrium limacinum* (IFO 32693); *Thraustochytrium* sp. 23B ATCC 20891; *Thraustochytrium striatum* ATCC 24473; *Thraustochytrium aureum* ATCC 34304); *Thraustochytrium roseum*(ATCC 28210; and Japonochytrium sp. L1 ATCC 28207. The recombinant host cells of the invention can also be a yeast cell, such as a yeast selected from the genus *Saccharomyces* or *Candida, Pichia, Yarrowia*, and *Kluveromyces lactis*.

In some embodiments the recombinant host cells of the invention can comprise at least one genetic modification. The at least one genetic modification can be any manipulation of a host cell's genome using the techniques of molecular biology or biotechnology. The genetic modification changes the genetic makeup of the cells, including the transfer of genes within and across species boundaries to produce improved or novel organisms. The at least one genetic modification can be, but is not limited to, the addition, deletion, modification, disruption, or optimization of a gene or portion of a gene. When one or more gene(s) is added it can be a heterologous gene. Any of the recombinant host cells of the invention can produce and comprise an antibody disclosed herein, which can be a functional and/or assembled antibody. In some embodiments the host cells overexpress the therapeutic protein (e.g., an antibody or antibody fragment), for example according to the titers disclosed herein.

Nucleic Acid Constructs

As used herein, the term "construct" is intended to mean any recombinant nucleic acid molecule such as an expression cassette, vector, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences has been linked in a functionally operative manner, i.e. operably linked. Constructs can also be non-naturally occurring (i.e., non-native).

The term "expression cassette" as used herein, refers to a nucleic acid construct that encodes a functional protein or functional RNA operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc. The present invention provides numerous examples of expression cassettes useful for producing the cells and proteins of the invention, and for use in the methods of the invention. The expression cassettes can be comprised in any construct operable in the host cells being utilized. Generally an expression cassette will comprise a promoter, an open reading frame (ORF) encoding the heterologous protein of interest, and a terminator. Additional features can include 3' and 5' homology arms from genomic DNA of the host cell. These can be useful for inserting or integrating the expression cassette at a specific locus in the genome of the cell. Any of the components or features of the expression cassette can be active in any of the host cells described herein. The functional protein can be a heterologous protein. An expression cassette can also comprise a signal sequence for secretion of the expressed protein from the cell.

As used herein, "exogenous" with respect to a nucleic acid or gene indicates that the nucleic or gene has been introduced ("transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

As used herein, "expression" refers to the process of converting genetic information of a polynucleotide into RNA through transcription, which is typically catalyzed by an enzyme, RNA polymerase, and, where the RNA encodes a polypeptide, into protein, through translation of mRNA on ribosomes to produce the encoded protein.

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "heterologous" when used in reference to a polynucleotide, a gene, a nucleic acid, a peptide or polypeptide, a protein, or an enzyme, refers to a polynucleotide, gene, a nucleic acid, polypeptide, protein, or an enzyme that is not derived from the host species. For example, "heterologous gene" or "heterologous nucleic acid sequence" as used herein, refers to a gene or nucleic acid sequence from a different species than the species of the host organism it is introduced into. A heterologous protein or peptide can be one encoded by a heterologous nucleic acid. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. Similarly, when referring to a protein localization sequence or protein domain of an engineered protein, "heterologous" means that the localization sequence or protein domain is derived from a protein different from that into which it is incorporated by genetic engineering.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrRNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

The nucleic acid molecules of the present disclosure will preferably be "biologically active" with respect to either a structural attribute, such as the capacity of a nucleic acid molecule to hybridize to another nucleic acid molecule, or the ability of a nucleic acid sequence to be recognized and bound by a transcription factor (or to compete with another nucleic acid molecule for such binding).

Nucleic acid molecules of the present disclosure include nucleic acid sequences of any length, including nucleic acid molecules that are preferably between about 0.05 kb and about 300 kb, or for example between about 0.05 kb and about 250 kb, or between about 0.05 kb and about 150 kb, or between about 0.1 kb and about 150 kb, or for example between about 0.2 kb and about 150 kb, about 0.5 kb and about 150 kb, or about 1 kb and about 150 kb.

The term "operably linked", as used herein, denotes a functional linkage between two or more sequences. For example, an operable linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous. Further, when used to refer to the joining of two protein coding regions, by "operably linked" is intended that the coding regions are in the same reading frame. Any of the promoters, terminators or other regulatory sequences disclosed herein can be operably linked to any of the SEQ ID NOs or other polynucleotide sequences disclosed herein.

The terms "promoter", "promoter region", or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked polynucleotide molecule such as, for example, a coding sequence of a polypeptide or a functional RNA sequence. Promoters may contain, in addition to sequences recognized by RNA polymerase and, preferably, other transcription factors, regulatory sequence elements such as cis-elements or enhancer domains that affect the transcription of operably linked genes. A "Labyrinthulomycetes promoter" as used herein refers to a native or non-native promoter that is functional in Labyrinthulomycetes cells. Any of the genes or SEQ ID NOs described herein can be under the control of or regulated by any of the promoters described herein.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. A recombinant cell contains a recombinant nucleic acid.

When applied to organisms, the terms "transgenic" "transformed" or "recombinant" or "engineered" or "genetically engineered" refer to organisms that have been manipulated by introduction of an exogenous or recombinant nucleic acid sequence into the organism. Non-limiting examples of such manipulations include gene knockouts, targeted mutations and gene replacement, promoter replacement, deletion, or insertion, as well as introduction of transgenes into the organism. For example, a transgenic microorganism can include an introduced exogenous regulatory sequence operably linked to an endogenous gene of the transgenic microorganism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

"Regulatory sequence", "regulatory element", or "regulatory element sequence" refers to a nucleotide sequence located upstream (5'), within, or downstream (3') of a polypeptide-encoding sequence or functional RNA-encoding sequence. Transcription of the polypeptide-encoding sequence or functional RNA-encoding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from untranslated regions (UTRs) from a particular polynucleotide sequence. Any of the regulatory elements described herein may be present in a chimeric or hybrid regulatory expression element. Any of the regulatory elements described herein may be present in a recombinant construct of the present disclosure.

The term "terminator" or "terminator sequence" or "transcription terminator", as used herein, refers to a regulatory section of genetic sequence that causes RNA polymerase to cease transcription.

The term "transformation", "transfection", and "transduction", as used interchangeably herein, refers to the introduction of one or more exogenous nucleic acid sequences into a host cell or organism by using one or more physical, chemical, or biological methods. Physical and chemical methods of transformation include, by way of non-limiting example, electroporation and liposome delivery. Biological methods of transformation include transfer of DNA using engineered viruses or microbes (for example, *Agrobacterium*).

Promoters and Terminators

The recombinant cell or organism of the invention can be any suitable organism but in some embodiments is a Labyrinthulomycetes cell, which can contain an expression cassette or expression vector described herein. The promoter (and/or terminator) sequences comprised on the expression cassette or vector can be any suitable promoter and/or terminator. Promoters and/or terminators can be used in any combination. For example, any promoter described herein or other promoters that may be isolated from or functional in Labyrinthulomycetes or derived from such sequences can be used in combination with any terminator described herein or other terminators functional in the recombinant cell or organism, or derived from such sequences. Functional promoters, terminators, and genetic elements are those able to perform their genetic purpose, for example, to initiate transcription of a DNA sequence. Functional terminators mediate transcriptional termination. For example, promoter and/or terminator sequences may be derived from organisms including, but not limited to, heterokonts (including Labyrinthulomycetes), fungi, microalgae, algae, yeast, and other eukaryotic organisms. In various embodiments the promoter and/or terminator is any one operable in a cell or organism that is a Labyrinthulomycetes, including any genus thereof. Any of the constructs can also contain one or more selection markers, as appropriate. A large number of promoters and terminators can be used with the host cells of the invention. Those described herein are examples and the person of ordinary skill with resort to this disclosure will identify other promoters useful in the invention. Examples of promoters include the alpha-tubulin promoter (tubαp), the TEFp promoter, Hsp60-788 promoter, Tsp-749 promoter, Tubα738 promoter, Tubα-997 promoter, a promoter from the polyketide synthase system, and a fatty acid desaturase promoter. Examples of useful terminators include pgk1, CYC1, and eno2. Promoters and terminators can be used in any advantageous combination and all possible combinations of promoter s and terminators are disclosed as if set forth fully herein.

In some embodiments the expression cassettes of the invention comprise one or more of 1) a polynucleotide encoding one or more signal sequences described herein; 2) a polynucleotide encoding one or more promoters; 3) a polynucleotide encoding one or more terminators; and 4) a polynucleotide encoding one or more proteins heterologous and/or exogenous to the host cell; 4) optionally, a polynucleotide encoding one or more selectable markers for screening on a medium or a series of media. The sequence encoding the heterologous protein can be operably linked to the promoter, or otherwise positioned to be regulated by the promoter. The promoter and terminator can be functional in a Labyrinthulomycetes cell. These components of an expression cassette can be present in any combination, and each possible sub-combination is disclosed as if fully set forth herein. In specific embodiments the signal sequences can be any described herein, but can also be other signal sequences that can be identified with reference to the present disclosure and which are also functional in the host cells. For example, the expression cassette or vector can encode a promoter and terminator sequences functional in *Aurantiochytrium*, a heterologous protein operably linked to the promoter, and a signal sequence having at least 90% sequence identity to any signal sequence described herein. In more embodiments the promoter can be an alpha-tubulin promoter or TEFp. The promoters can be paired with any suitable terminator, but in specific embodiments the tubαp can be paired with the pgk1t terminator. In another embodiment the TEFp promoter can be paired with the eno2 terminator, both terminators being from *Saccharomyces cerevisiae* and also being functional in Labyrinthulomycetes. In another embodiment the promoter can be TEFp and the terminator can be pgk1 or CYC1. In another embodiment the promoter can be Hsp60-788 and the terminator can be pgk1, CYC1, or eno2. In another embodiment the promoter can be Tsp-749 and the terminator can be pgk1, CYC1, or eno2. In another embodiment the promoter can be Tubα-738 and the terminator can be pgk1, CYC1, or eno2. In another embodiment the promoter can be Tubα-997 and the terminator can be pgk1, CYC1, or eno2. In another embodiment the promoter can be from the polyketide synthase system, and the terminator can be pgk1, CYC1, or eno2. In another embodiment the promoter can be a fatty acid desaturase promoter and the terminator can be pgk1, CYC1, or eno2. The selectable marker can be any suitable selectable marker or markers but in specific embodiments it can be nptII or hph. In one embodiment nptII can be linked to the heavy chain constructs and hph can be linked to the light chain constructs.

Figure 1:
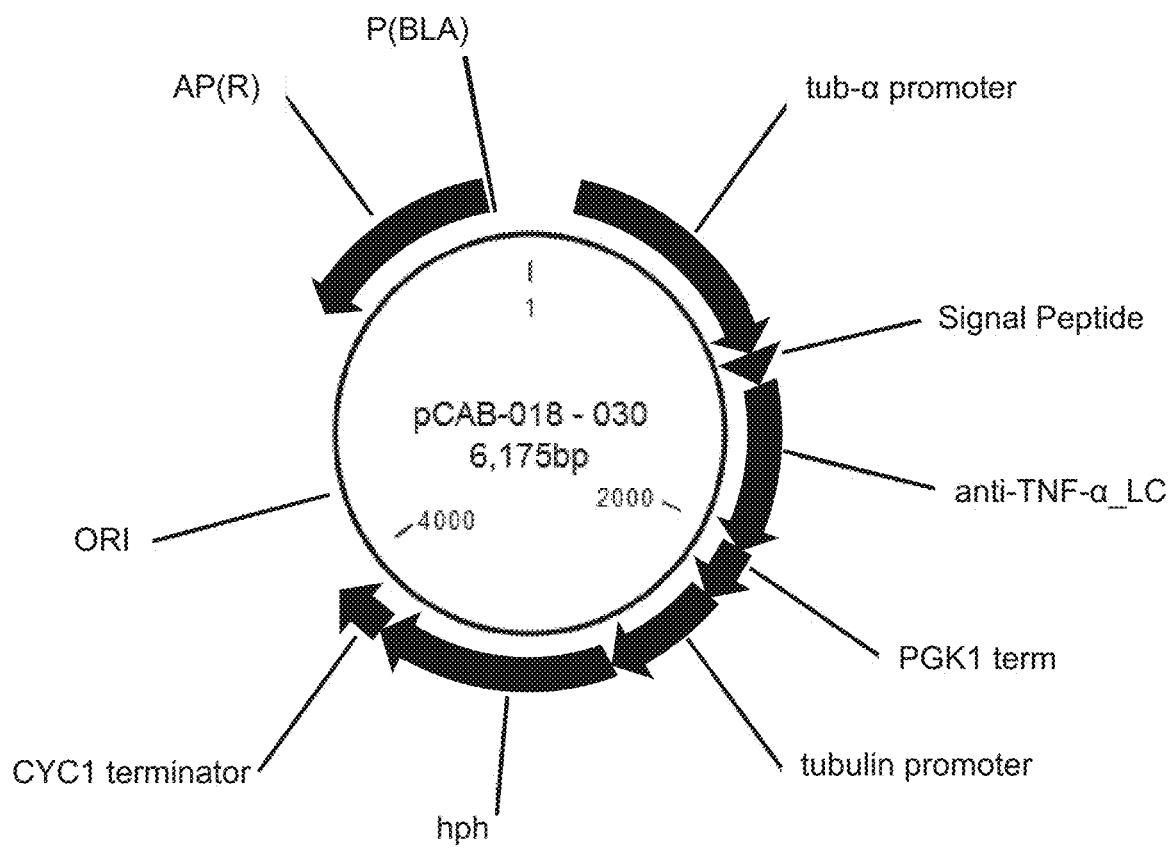
Figure 2:
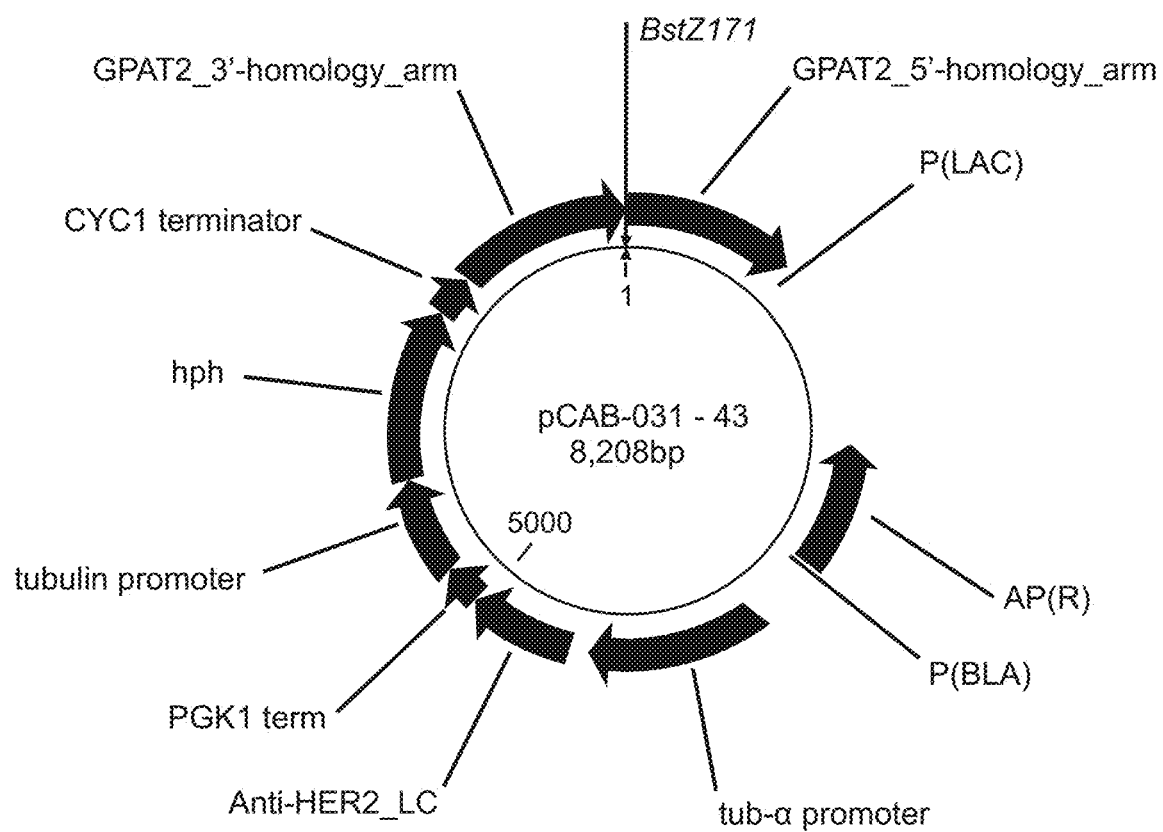

FIG. 1 provides an illustration of specific examples of an expression cassettes useful in the invention. The tubulin-alpha promoter drives the expression of the mature light chain of anti-TNF-alpha antibody with a variety of signal peptides. pCAB030 is a version of these constructs where an ATG was introduced at the start of the ORF, but no signal peptide. All these constructs also carry the hph marker for selection on hygromycin B plates. FIG. 2 is an illustration of a general map of pCAB-031-043, with each serial number relating to a different signal sequence. pCAB031-043 are versions of pCAB018-030 where sequences were introduced to allow for directed integration at the GPAT2 locus via homologous recombination. The 5' and 3' homology arms were amplified from chytrid genomic DNA using primer pairs having 5' extensions that introduced sequences to allow for Gibson Assembly® cloning at the SbfI site of plasmids pCAB018-029. Other primers had 5' extensions that introduced complementary sequences to allow for Gibson Assembly®. In addition, the primers were designed to introduce a unique BstZ17I site. The 5' and 3' homology arms were combined with the SbfI digested pCAB018-030 in a Gibson Assembly® reaction to yield pCAB031-043.

The host cell or organism can comprise a vector or expression cassette of the invention described herein. The vector or expression cassette can be inserted or otherwise integrated into the genome of the cell or organism, or integrated into other DNA of the cell or organism. In other embodiments the vector or expression cassette can also be present within the cell or organism without being integrated in the genome, for example present on a vector or plasmid. In some embodiments the vector or expression cassette can be multiplied in the cell or organism and/or passed during cell division.

Therapeutic Proteins and Peptides

The host cells of the invention can produce a variety of functional heterologous proteins or peptides, such as therapeutic peptides or proteins, or fragments of any of them, that are encoded on the expression vectors or cassettes of the invention. Therapeutic peptides or proteins are those peptides and proteins that are useful in the treatment or alleviation of a disease or medical condition in a human or animal patient. Such use is more than merely nutritional and performs an action on targets in the human or animal body resulting in the treatment or alleviation of the disease or medical condition and examples are provided herein. But any protein or peptide can be produced according to the invention. The proteins or therapeutic proteins produced by the host cells of the invention can be heterologous to or homologous to the host cell. In some embodiments the therapeutic peptide or protein of the invention is an antibody or portion thereof, for example the light chain, heavy chain, or both of an antibody, or one or more single-chain variable fragment(s) (scFvs) of an antibody, or a bi-specific antibody.

Antibodies are immune system-related proteins called immunoglobulins. Each antibody consists of four polypeptides—two heavy chains and two light chains joined to form a "Y" shaped molecule. The antibodies can thus form a tetrameric quartenary structure. The amino acid sequence in the tips of the "Y" can vary greatly among different antibodies, providing the variable region. This variable region provides the antibody specificity for binding an antigen. The variable region includes the ends of the light and heavy chains. In some embodiments the antibodies of the invention are composed of a heavy chain (HC) and a light chain (LC), and thus require both genes that encode the two chains to be expressed. The antibodies of the invention can be assembled antibodies, meaning that the antibody comprises a light chain and a heavy chain, and they can be covalently bound to each other as a whole antibody. In some embodiments the antibodies of the invention are IgG antibodies. The antibodies of the invention can be composed of four peptide chains, including two identical heavy chains and two identical light chains. The antibodies can have two antigen binding sites. The two heavy chains can be linked to each other and to a light chain by disulfide bonds and have two identical halves that form the Y-like shape and contain identical antigen binding sites. The antibodies can also be multimeric antibodies, and can also have binding activity to more than one epitope. It was unexpectedly discovered that the cells of the invention engineered as described herein express a light chain and a heavy chain of an antibody molecule and can also assemble the light chain and heavy chain into a complete, assembled antibody molecule, such as any of those described herein. The cells can also secrete the light chain and heavy chain of the antibody, or the assembled antibody molecule.

In some embodiments the therapeutic protein of the invention can be an antibody, such as a functional antibody or a functional fragment of an antibody. In various embodiments the antibody can have an amino acid sequence of eculizumab, natalizumab, cetuximab, omalizumab, usteinumab, panitumumab, denosumab, trastuzumab or adalimumab (anti-TNF-alpha antibody), or a functional fragment of any of them. The antibody can also be any anti-TNF-alpha antibody or an anti-HER2 antibody, or a functional fragment thereof. Each of these proteins is an antibody and a therapeutic protein, as well as a monoclonal antibody. The therapeutic protein can also be any IgG2 or IgG4 antibody or fragment thereof. The heterologous proteins encoded by the expression vectors or cassettes of the invention can bind to any antigen, with examples including TNF-alpha and HER2.

Trastuzumab (Herceptin®) is an anti-HER2 monoclonal antibody that interferes with the HER2/neu receptor and is useful in the treatment of certain breast cancers. The HER receptors are proteins that are embedded in the cell membrane and communicate molecular signals from outside the cell (EGFs) to inside the cell, and turn genes on and off. The HER protein, Human Epidermal Growth Factor Receptor, binds to Human Epidermal Growth Factor, and stimulates cell proliferation. In some cancers, notably certain types of breast cancer, HER2 is over-expressed, and causes cancer cells to reproduce uncontrollably. Adalimumab (Humira®) is an anti-TNF-alpha monoclonal antibody useful as a TNF inhibiting anti-inflammatory medication and used to treat various ailments such as arthritis, Crohn's disease, colitis, among other diseases. Adalimumab binds to tumor necrosis factor-alpha (TNFα). TNFα normally binds to TNFα receptors, which leads to the inflammatory response of autoimmune diseases. By binding to TNFα, adalimumab reduces this inflammatory response. A functional antibody or antibody fragment is a molecule that is an antibody or antibody fragment that binds to a target epitope and thereby produces a desired response, for example a biological response or action, or the cessation of a response or action). The desired response can be the same as the response to a natural antibody, but the response can also be to mimic or disrupt the natural biological effects associated with ligand-receptor interactions. When the protein is a functional antibody fragment it can comprise at least a portion of the variable region of the antibody or can comprise a portion of or the entire antigen binding site of an antibody, and therefore can perform the antigen binding properties that are similar to or the same in nature and affinity to those of the complete antibodies. Any of the recombinant cells disclosed herein can comprise a functional and/or assembled antibody molecule described herein, or a functional fragment thereof. And any of the expression vectors or cassettes described herein can encode such a functional antibody or functional fragment thereof. Any type of heterologous protein or antibody or antibody fragment can be produced in the present invention. Examples include IgG2 or IgG4 or subunits of immunoglobulins, for example the kappa subunit.

When the heterologous protein is an antibody, the antibody can have a light chain and a heavy chain, either or both of which can bind to any antigen described herein, including but not limited to the HER2 receptor or TNF-alpha. The antibody can also have at least 70% or at least 80% or at least 90% or at least 95% or at least 97% or at least 98% or at least 99% or 85-99% or 90-99% or 95-99% sequence identity with an amino acid sequence of any therapeutic protein or protein fragment described herein, e.g. any of SEQ ID NO: 1-8. The antibody can have a light chain and a heavy chain having any combination of said sequence identities to SEQ ID NO: 1 and 2; or SEQ ID NO: 3 and 4; or SEQ ID NO: 5 and 6; or SEQ ID NO: 7 and 8, as the light chain and heavy chain, respectively. For example, the antibody could have at least 90%/sequence identity to SEQ ID NO: 1 and at least 95% sequence identity to SEQ ID NO: 2, and so on. The therapeutic protein can also be a functional fragment of an antibody described herein. A functional fragment is a portion of the full antibody or therapeutic protein that nevertheless has at least 85% or at least 90% or at least 95% of the relevant activity of the full antibody or therapeutic protein. It can also have at least 200 or at least 400 or at least 500 or at least 550 or at least 600 or at least 800 or at least 1000 or at least 1200 or at least 1300 contiguous amino acid residues to any of SEQ ID NO: 1-8 and also have said activity. Any of the therapeutic proteins or antibodies described herein (or functional fragment of any), or combinations thereof described herein, can also have at least one substitution modification versus SEQ ID NO: 1-8.

In some embodiments the heterologous or therapeutic protein is a bi-specific T cell engager antibody. These are bispecific antibodies that are fusion proteins having two single-chain variable fragments (scFvs) of different antibodies, or amino acid sequences from four different genes on a single peptide chain (e.g. of about 55 kDa). Bispecific T cell engagers can comprise an scFvs that binds to a T cell antigen (e.g. the CD3 receptor) and the other scFvs can bind to a tumor-specific antigen molecule. As shown herein, these bispecific T cell engagers can also be encoded by the expression cassettes or vectors of the invention. In various embodiment one of the scFvs can bind to a T cell antigen and the other anti-CD19, anti-CD3, anti-CD38, or prostate-specific membrane antigen (PSMA).

The invention also provides methods of producing any heterologous or therapeutic protein described herein by cultivating a host cell of the invention in a suitable culture medium. The host cell can contain an expression cassette as described herein and can encode any functional signal sequence described herein that directs the secretion of the heterologous protein from the cell and into the growth medium. The heterologous protein can be harvested from the culture. In some embodiments the production method is a continuous production method or a continuous culture method, meaning that the protein can be harvested from the growth medium and the growth medium replenished without stopping or interrupting the culture and the production of the protein.

Growth of the host cells can be conducted in any convenient bioreactor or other vessel for growing cell cultures, including both small scale and large scale vessels. Cell cultures can be grown in any convenient vessel, system, or continuous culture device. Examples include, but are not limited to, a shake flask, a chemostat, a cytostat, an auxostat, a turbidostat, or a retentostat. A chemostat is a bioreactor to which fresh medium is continuously added, while culture liquid containing left over nutrients, metabolic end products, and microorganisms are continuously removed at the same rate to keep the culture volume constant. In any of the vessels a physiological steady state under constant culture parameters can be achieved and continuous growth maintained at a specific growth rate. By changing the rate with which medium is added to the bioreactor the specific growth rate of the host cells or culture can be easily controlled. In various embodiments culture parameters can include any one or more of culture volume, flow rate of medium into (feed) and/or out of (effluent) the vessel, dilution rate, dissolved oxygen concentration, nutrient concentration, sugar concentration, product concentration, pH, and cell density. Thus, in some embodiments a constant inward flow of fresh medium can be maintained at a rate equal to a constant outward flow of the cell culture. In this way, the culture can be continuously diluted and continuously grows (divides) where the growth (rate of cell division) of the culture is directly related to the rate of culture dilution. Thus, the rate of cell division can be adjusted by adjusting the culture dilution rate, and variants that have a growth advantage under the selective condition become enriched in the culture as poorer growing cells "wash out" through continuous dilution of the culture. In some embodiments one or more of (or all of) the culture conditions are held constant. In some embodiments culture liquid is removed from the bioreactor but biomass is retained on a filter (e.g. a retentostat).

A cytostat is similar to a chemostat, except that the culture is maintained at a cell density well below that at which nutrient limitation could occur. Dilution of the cytostat occurs based on cell density of the culture, which is monitored at regular intervals or continuously based on the determination of the cell concentration and/or the single cell property distribution of the growing cell populations. The culture can be monitored and controlled by an automated flow cytometer. The flow cytometer can be integral to the cytostat apparatus (see, for example, U.S. Pat. No. 7,901,937). Because cytostat cultures do not approach nutrient limitation nor experience any significant accumulation of fermentation products that may affect growth, cytostat cultures are considered to be in a steady state of growth and can be grown even at very low cell concentrations. The culture parameters can be precisely defined by the feed composition since products of cell growth may not be present in significant amounts, and therefore effects on cell growth of various culture parameters can be easily determined. Because the dilution rate is calibrated to the cell division rate, cells can be allowed to proliferate without excessive dilution until cells begin to achieve a certain density.

In various embodiments the bioreactor can be of any volumetric capacity. For microbial strains such as fungi and chytrids, for example, culturing can be in a bioreactor (e.g., a chemostat or cytostat) having a fermenter volumetric capacity of from about 25 mL to about 10 L, and can be from 200 mL to about 5 L, or from about 300 mL to about 2 L, or from about 400 mL to about 1 L or from 300 ml to about 3 L or from about 5 L to about 10 L or more than 10 L. The culture period can be for any length of time, such as for example, from one day to several months. Preferably, for fungi and chytrids, the culturing period in the bioreactor is for a period of time greater than one day, for example, for a period of from about 2 days to about 30 days, or from about 3 days to about 20 days, or from about 4 days to about 15 days. In some embodiments cytostat selection is preferred. In a cytostat, the culture period can in some embodiments, for example, be from about 3 days to about 10 days.

Single colonies of the microorganism can be isolated by dilution plating or flow cytometry from cultures grown for any period of time and the resulting isolate or isolates can be screened for any desirable properties. For example, an isolate can be tested for any one of or any combination of: increased growth rate, increased biomass accumulation, increased lipid, fatty acid, or protein production rate, increase antibody production rate, increased triglyceride production rate, increased total lipid accumulation, increased FAME accumulation, increased triglyceride accumulation, increased FAME production rate, increased DHA production rate, increased DHA accumulation, increased DHA as a percentage of fatty acids, increased ratio of DHA to DPA, etc. Any feasible methods for determining protein, antibody, lipid, or fatty acid amounts can be employed. The testing can be under any culture conditions, including those listed hereinabove that may be used in culturing a strain prior to testing, for example, using particular carbon or nitrogen sources or concentrations, salt concentration, temperature, pH, etc.

Signal Peptides

A signal peptide (or signal sequence) is a short peptide, usually located at the N-terminus of a newly synthesized protein. These sequences direct the newly synthesized protein (usually to the endoplasmic reticulum) for secretion from the cell and into the growth medium. Signal peptides, or a functional fragment thereof, can have at least 5 or at least 10 or at least 15 or at least 20 or at least 25 amino acids, or from 5-30 or from 5-40 or 5-50 amino acids or from 5-35 or 5-25 or 5-20 or 10-20 or 10-25 or from 25-50 or from 3-12 or 3-15 amino acids, which in some embodiments can be any consecutive amino acid sequence of said length from any one of SEQ ID NO: 9-94.

The present invention also provides signal peptides and nucleic acid molecules that encode signal peptides useful in a host organism of the invention. Any suitable signal peptide can be utilized in the invention. Signal peptides or signal sequences can direct the secretion of a protein (e.g., a heterologous protein) from a host cell, i.e. they can be functional signal peptides or signal sequences. Signal peptides useful in the invention have secretion signal activity in a host cell of the invention. Examples of signal peptides useful in the invention are provided in the amino acid sequences of SEQ ID NOs: 9-94, or a functional fragment of any of them. A functional fragment of a signal peptide is a fragment that is less than the full length peptide but nevertheless directs the secretion of a protein (e.g., the protein encoded by the vector or expression cassette) from the cell.

Signal peptides of the invention can be any peptide having at least 70% or at least 75% or at least 80% or at least 85% or at least 90% or at least 92% or at least 95% or 70-99% or 80-99% or 85-99% or 90-99% or 95-99% sequence identity with any of the amino acid sequences disclosed herein (e.g. amino acids of SEQ ID NO: 9-94), or a functional fragment thereof; signal peptides can also be encoded by a nucleic acid sequence having at least 70% or at least 75% or at least 80% or at least 85% or at least 90% or at least 92% or at least 95% or 70-99% or 80-99% or 85-99% or 90-99% or 95-99% sequence identity with any of the nucleic acid sequences disclosed herein (e.g. SEQ ID NO: 21-32 or 48-67 or 79-94), or a functional fragment thereof, which functional fragment can be any sequence of at least 100 or 120 or 150 or 200 consecutive nucleotides. Signal peptides, or a functional fragment thereof, can also have at least 5 or at least 7 or at least 10 or at least 15 or at least 20 or at least 25 or at least 35 or at least 40 or at least 45 or at least 50 contiguous amino acid residues to any of the amino acid sequences disclosed herein. Any of the signal peptides or sequences, or functional fragment thereof, can also have at least one substitution modification versus any of the sequences disclosed herein. In various other embodiments the signal sequence can have at least two or at least three or at least four or at least five or at least six or at least seven or at least eight or at least nine or at least 10 or 1-3 or 3-5 or 5-7 or 7-9 or 1-10 substitution modifications versus an amino acid sequence disclosed herein. Signal sequences can also be encoded by a nucleic acid having at least one substitution modification versus any of the nucleic acid sequences disclosed herein. In various embodiments the signal sequence can be encoded by a nucleic acid having at least two or at least three or at least four or at least five or at least six or at least seven or at least eight or at least nine or at least 10 or 1-3 or 3-5 or 5-7 or 7-9 or 1-10 or 10-20 or 1-50 or 1-75 or 1-100 substitution modifications versus a nucleic acid sequence disclosed herein. Functional fragments of these sequences are also disclosed, and can have at least 15 or at least 20 or at least 25 or at least 50 or at least 100 nucleotides contiguous to any amino acid or nucleic acid sequence disclosed herein.

SEQ ID NO: 9-20 are encoded by SEQ ID NO: 21-32. SEQ ID NO: 33-47 are encoded by SEQ ID NO: 48-62. SEQ ID NO: 63-78 are encoded by SEQ ID NO: 79-94. Any of the nucleic acid sequences disclosed herein can be comprised in an expression vector or expression cassette. Expression vectors can comprise any of the expression cassettes disclosed herein. Expression vectors or expression constructs can be plasmids or other constructs and are designed for gene expression in host cells. Expression vectors or constructs can be used to introduce sequences of the invention into target cells and can utilize the cell's mechanisms for expression of proteins or peptides to produce the protein or peptide in the host cell. The expression cassettes of the invention comprising sequences of the invention can also be introduced into cells as circular or linear DNA and be incorporated into the genome of the organism and function from that location on the genome. The expression vectors or expression cassettes of the invention can also contain additional sequences for propagation and/or expression of the sequences in the chosen host cell type.

Non-limiting examples of a substitution modification for a signal peptide or a therapeutic protein (e.g. antibody) described herein can include a substitution, an insertion, a deletion, a rearrangement, an inversion, a replacement, a point mutation, and a suppressor mutation in the encoding DNA, which can result in a change in the encoded amino acid sequence. Methods of performing substitution modifications are known in the art and are readily available to the artisan such as, for example, site-specific mutagenesis, PCR, and gene synthesis. Non-limiting examples of substitution modification methods can also be found in Maniatis et al., (1982) Molecular Cloning: a Laboratory Manual; Cold Spring Harbor Laboratory, Cold Spring Harbor, N.Y. In some embodiments the substitution modification(s) do not substantially alter the functional properties of the resulting nucleic acid fragment or protein/peptide relative to the initial, unmodified fragment. It is therefore understood, as those skilled in the art will appreciate, that the disclosure encompasses more than the specific exemplary sequences. A substitution modification can also include alterations that produce silent substitutions, insertions, deletions, etc. as above, but do not alter the properties or activities of the encoded protein or how the proteins are made.

The degree of amino acid or nucleotide sequence identity can be determined by various computer programs for aligning the sequences to be compared based on designated program parameters. For example, sequences can be aligned and compared using the local homology algorithm of Smith & Waterman *Adv. Appl. Math.* 2:482-89, 1981, the homology alignment algorithm of Needleman & Wunsch *J. Mol. Biol.* 48:443-53, 1970, or the search for similarity method of Pearson & Lipman *Proc. Nat'l. Acad Sci. USA* 85:2444-48, 1988, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al., *J. Mol. Biol.* 215:403-10, 1990, is publicly available through software provided by the National Center for Biotechnology Information. This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., 1990, supra). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. See, Henikoff& Henikoff, *Proc. Nat'l. Acad. Sci.* USA 89: 10915-19, 1989.

In addition to calculating percent sequence identity, the BLAST algorithm also performs a statistical analysis of the similarity between two sequences (see, e.g., Karlin & Altschul, *Proc. Nat'l. Acad Sci.* USA 90:5873-87, 1993). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

Titers

Another advantage of the cells and methods of the invention is that therapeutic or heterologous proteins can be produced in host cells, such as Labyrinthulomycetes cells, in high titers. In some embodiments the heterologous protein can be produced in culture having a titer, expressed as mg/ml produced in a 24 hour period, of at least 5 mg/L of culture or at least 6 mg/L of culture or at least 7 mg/L culture or at least 9 mg/L or at least 11 mg/L or at least 12 mg/L or at least 15 mg/L or at least 17 mg/L or at least 18 mg/L or at least 19 mg/L or at least 20 mg/L or at least 25 mg/L or at least 30 mg/L or at least 35 mg/L or at least 40 mg/L or at least 45 mg/L or at least 50 mg/L or at least 55 mg/L or at least 60 mg/L or 5-15 mg/L or 5-16 mg/L or 5-17 mg/L or 5-18 mg/L or 5-20 mg/L or 15-25 mg/L or 20-30 mg/L or 30-40 mg/L or 40-50 mg/L or 50-60 mg/L or 60-80 mg/L or 80-100 mg/L of culture in a 24 hour period. The heterologous protein produced can be any described herein, and in some embodiments the heterologous protein is an antibody, which can comprise a heavy chain and a light chain.

Example 1—Expression of Anti-TNF-Alpha Antibody Light Chain

This example shows the expression of the light chain of the anti-TNF-alpha antibody. An *Aurantiochytrium* sp. host cell was utilized with SEQ ID NOs: 9-20 as example signal sequences. Each of these peptides were cloned at the 5' end of a sequence encoding the mature anti-TNF-alpha antibody light chain in the construct of FIG. 1 (pCAB018). Control constructs had no signal peptide. Another set of constructs were made containing each of the signal peptides and also with homology arms to target integration at the GPAT2 locus (FIG. 2). This was done to avoid positional effects. These constructs were designed to introduce a unique BstZ17I site between the 5' and 3' homology arms such that the 5' to 3' linearized product would be configured as follows: 5' homology arm, the expression cassette, 3' homology arm.

Genome editing techniques were utilized to insert the pCAB vector at the GPAT2 site. The transformants were screened for correct integration of the cassette at the GPAT2 by 1) qPCR for deletion of GPAT2, 2) colony PCR for 5' and 3' junctions between the cassette and the external genomic sequence, and 3) qPCR for similar copy numbers across transformants using primers targeting the light chain sequence.

Figure 4:
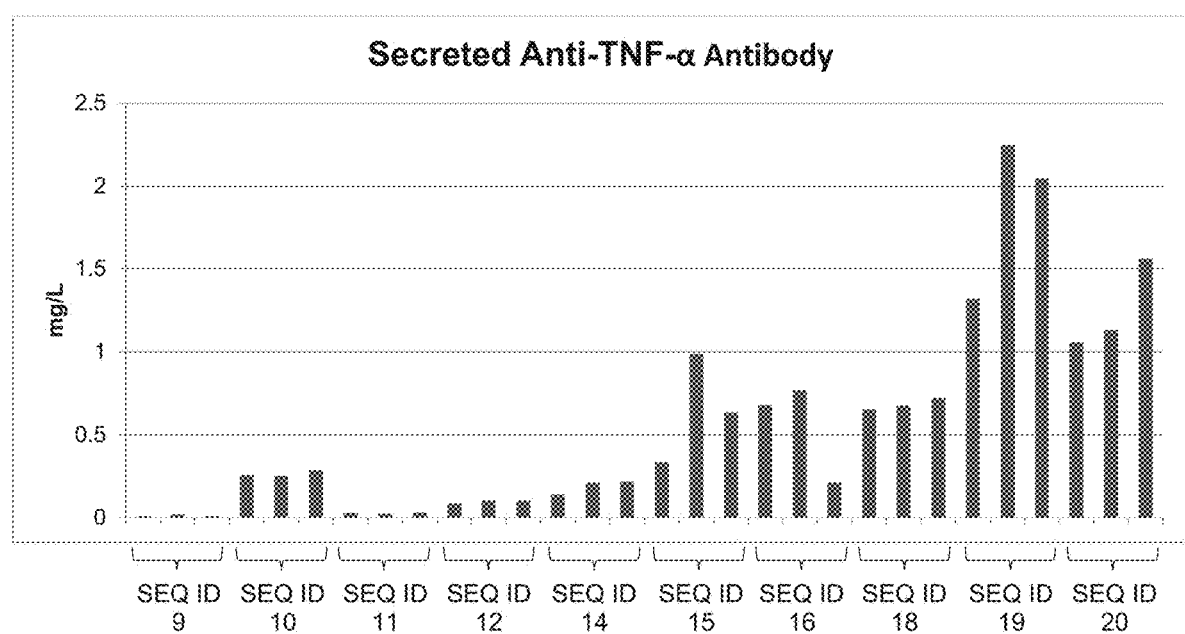
FIG. 4 is a bar graph showing supernatant titers of secreted anti-TNF-alpha antibody light chain, using various signal peptides.

Transformants for each signal peptide construct were analyzed in triplicate and examined for secretion of anti-TNF-alpha antibody light chain. Each clone was cultured overnight in 3 mL FM2 (17 g/L aquarium salt, 10 g/L yeast extract, 10 g/L peptone, 20 g/L dextrose) in a 24-well plate. They were then diluted 1000× into fresh FM2 (3 mL) and incubated for about 24 hours. The cells were pelleted by centrifugation (2000 g×5 min) and the supernatants assayed for the presence of light chain by LC-capture/LC-detect sandwich ELISA. The results are shown in FIG. 4. It was also verified that the differences in titers were not due to differences in expression levels by performing RNA extraction and analysis by PCR and comparing the results with those from LC-capture/LC-detect sandwich ELISA assay. Results indicated that the differences in titer were not due simply to differences in gene expression.

Example 2—Expression and Secretion of Anti-HER2 and Anti-TNF-Alpha HC and LC

Constructs containing expression vectors with the sequences of anti-TNF-alpha heavy chain (SEQ ID NO: 2) and light chain (SEQ ID NO: 1), and with anti-HER2 heavy chain (SEQ ID NO: 4) and light chain (SEQ ID NO: 3) were cloned. Signal sequences (SEQ ID NOs: 11 and/or 19) were also cloned in vectors containing each of the heavy chain or light chain sequences, with alpha-tubulin as the promoter and pgk1t as the terminator. hph and nptII were used as selection markers.

Constructs containing the sequence for the heavy chain and light chain for each antibody were linearized and then co-transformed into *Aurantiochytrium* sp. Constructs were selected for on paromomycin medium and then hygromycin to select for cells containing both a light chain and a heavy chain sequence. Diagnostic PCR identified clones that contained full length heavy chain and light chain expression cassettes, and numerous clones were identified. Results were confirmed by PCR on genomic DNA and RNA expression of the cassettes was also confirmed by PCR.

Figure 3:
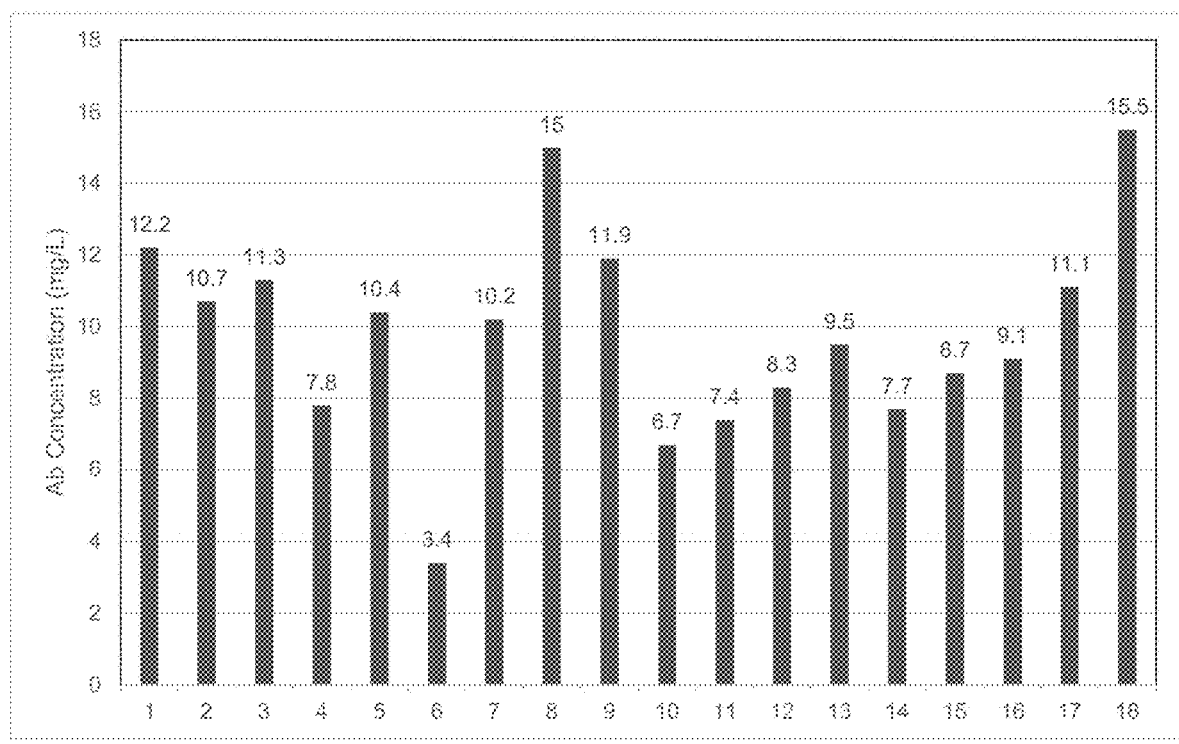

ELISA screening was performed on the clones transformed with expression cassettes and that utilized the tubαp. Clones were grown for about 20 h at 30° C. and 225 rpm and then back diluted into fresh medium and grown for about 20 hours in the same conditions. Cells were removed by centrifugation. The ELISA method utilized an HC capture and an LC detect sandwich assay that provided a positive signal only if both the HC and LC were present as a complete antibody. FIG. 3 illustrates that antibody supernatant titers in the mg/L range were obtained for clones having heavy and light chains. The first 16 clones contained heavy and light chains of anti-TNF-alpha and clones 17 and 18 secrete anti-HER2. As illustrated in the bar graph almost all of the clones making anti-TNF-alpha had a titer of greater than 7.0 mg/L. Both of the clones for anti-HER2 had a titer of greater than 10 mg/L. It was also noted that culture OD had a positive relationship with the antibody titer with a higher OD indicating a higher antibody titer. This experiment was repeated with TEFp as promoter and a similar result was obtained with some clones giving titers as high as greater than 20 mg/L or greater than 25 mg/L or greater than 30 mg/L. It was therefore demonstrated that the cells of the invention are able to produce a heavy chain and light chain of an antibody molecule, and to assemble them into a whole antibody.

Example 3—Binding of Anti-HER2 Antibody Produced by Labyrinthulomycetes

Figure 5:
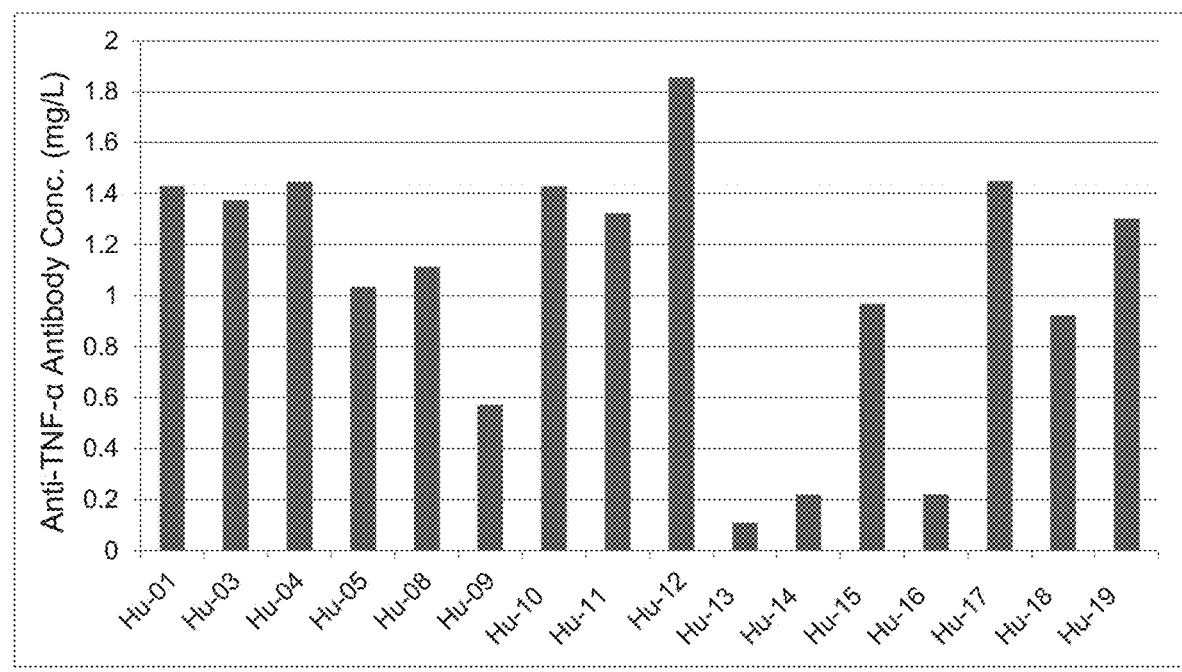
FIG. 5 is a graph illustrating calculated concentrations of anti-TNF-alpha antibody that binds TNF-alpha from the supernatants of Labyrinthulomycetes (here *Aurantiochytrium* sp.) cultures. SEQ ID NO: 19 was the signal sequence for Hu-01, 03, 04, 10-19 were used as signal sequences.

This Example shows that antibody made in a host cell (*Aurantiochytrium*) binds to a recombinant form of the receptor tyrosine-protein kinase erbB-2 (Her2). Neat samples and seven half-log serial dilutions of each sample were added to a 96 well plate that was incubated overnight with 5 ug/ml of recombinant Her2 as described above. The recombinant protein consists of 397 amino acids that represent the extracellular domain of the native receptor. The assay is a solid phase ELISA based on the sandwich principle performed in a 96 well plate. Buffer was 20×TBS Tween® 20 buffer. Samples were incubated in a plate coated with recombinant Her2 (human ErbB-2). Following a wash step, an HRP conjugated secondary antibody (anti-human IgG Fc (HRP)) was introduced and bound to human IgG (FIG. 5).

Example 4—Binding of Anti-TNF-Alpha Antibody Produced by Labyrinthulomycetes

This assay quantitates the amount of antibody present in solution that can bind to Tumor Necrosis Factor alpha (TNFα). A solid phase ELISA "sandwich" assay was utilized. Standards and diluted samples were incubated in a plate coated with TNF-alpha, followed by a wash step and then incubation with an HRP conjugated probe.

The assay was performed at room temperature (22-26° C.) and samples were assayed in duplicate and read on a microplate reader at 450 nm. Raw data is expressed in absorbance units. A standard curve was generated for each assay and the anti-TNF-alpha concentrations (mg/L) calculated from the standard curve equation. The upper limit of detection was defined as 1000 mg/L and the lower limit as less than 30 mg/L.

FIG. 6 illustrates data from an ELISA using supernatants from Labyrinthulomycetes (*Aurantiochytrium*) cultures expressing anti-TNF-alpha antibody. All clones had calculated values of antigen binding antibody that fell within the range of the standard curve. The data show that the anti-TNF-alpha produced as described herein binds the target antigen, TNF-alpha.

Example 5—Anti-HER2 Functional Antibody Assay

Agonist and antagonist activity was examined for control compounds and anti-HER2 produced in the above Examples at the human epidermal growth factor receptor 2 (Her2). HER2 (also referred to as Erbb2) is a member of the human epidermal growth factor receptor (HER/EGFR/ERBB) family and a receptor tyrosine kinase (RTK). These receptors form homo/hetero dimers upon activation, resulting in the phosphorylation of tyrosine residues within the cytoplasmic domain. This process activates a variety of signaling pathways that ultimately result in maintaining cell survival, proliferation, and differentiation.

One important mechanism used by anti-HER2 to kill targeted tumor cells is Antibody-Dependent Cell-Mediated Cytotoxicity (ADCC), a process by which antibody bound cells are targeted for destruction by components of the cell-mediated immune system, such as natural killer cells. The ADCC reporter bioassay is a bioluminescent reporter assay for quantifying biological activity on pathway activation by therapeutic antibody drugs in an ADCC mechanism of action (MOA) assay. The effector cells used in this assay is an engineered Jurkat cells stably expressing the FcγRIIIa receptor (V158 variant) that binds the Fc region of antibodies bound to target cells and an NFAT response element driving expression of firefly luciferase. Antibody biological activity in ADCC MOA is quantified through the luciferase produced as a result of NFAT pathway activation. This is a surrogate read out for Her2 mediated cytotoxicity, and can be used as a direct measurement of antibody efficacy.

Purified antibody from *Aurantiochytrium* cultures was tested for ADCC using the Her2 expressing human breast cancer cell line, BT-474 (ATCC® HTB-20™), as target cells. Antibody was added to target cells at various concentrations in the presence of recombinant effector cells and incubated for 6 hrs as described in the manufacturers protocol (Promega®). Luciferase activity in the effector cells was quantified with luminescence readout (RLU). The calculated EC50 value for Anti-HER2 was 0.061 mg/L. Two control antibodies, Anti-TNFα produced in *Aurantiochytrium*, and a commercially available human IgG produced no response. FIG. 7 shows a dose response curve demonstrating the functional binding of anti-HER2.

Example 6—Anti-TNF-Alpha Functional Assay

The assay shows the inhibitory effect of anti-TNF-alpha in a cell based functional assay. Anti-TNF-alpha binds to free Tumor Necrosis Factor alpha (TNF-alpha) and blocks its ability to bind to TNF-alpha receptors. Upon activation, TNF-alpha receptors trigger a downstream signaling cascade that induces release of inflammatory cytokines and/or apoptosis. Anti-TNF-alpha is expressed in *Aurantiochytrium* and the functional action of these antibodies in their ability to block TNF-alpha activity in vitro is demonstrated.

Anti-TNF-alpha inhibition of action was analyzed in a mouse fibroblast cell line (L929). The cells were exposed to TNF-alpha for 0-48 hours to stimulate cytokine production or cell death in the presence or absence of anti-TNF-alpha purified from the culture supernatant of *Aurantiochytrium*. Cell cytotoxicity was measured indirectly by using the CellTiter-Glo® Luminescent Cell Viability Assay (Promega®). FIG. 9 shows a concentration dependent effect of anti-TNF-alpha on TNF-alpha induced killing of the cells.

Example 7—Expression of Anti-CD19/Anti-CD3 Bi-Specific T-Cell Engager

This example shows the expression of the anti-CD19/anti-CD3 bi-specific T-cell engager antibody. An *Aurantiochytrium* sp. host cell was utilized with SEQ ID NO: 63-78 as signal sequences. Each of these peptides were cloned at the 5' end of a sequence encoding the mature anti-CD19/anti-CD bi-specific T-cell engager antibody in the construct of FIG. 9. The bi-specific T-cell engager antibody was expressed using the TEF promoter derived from the host organism. The control construct utilized the signal peptide of SEQ ID NO: 19.

The host strain was transformed with these constructs as circular plasmids. Transformants were screened for integration of the cassette based on homologous recombination within the TEFp sequence by colony PCR for 5' and 3' junctions between the cassette and external genomic sequence. In addition, transformants were screened by qPCR for similar copy numbers across transformants using primers targeting the bi-specific T-cell engager antibody.

Three independent transformants for each signal peptide construct were analyzed for secretion of anti-CD19/anti-CD3 antibody. Each clone was cultured overnight in FM2. They were then diluted 1000× into fresh FM2 and incubated for approximately 24 hours. The cells were pelleted by centrifugation and the supernatants assayed for the anti-CD19/anti-CD3 antibody by western blot analysis. Western blots were probed with an anti-His antibody and detected using an HRP-conjugated anti-mouse antibody and ECL-Plus™ substrate. Chemifluorescence was detected and band volumes calculated using a laser scanner. Band volumes were normalized to the control (SEQ ID NO: 19) and averaged (Table 1). These results show that the sequences direct the secretion of heterologous proteins.

TABLE 1

| Signal Peptide | Band density, relative to SEQ ID NO: 19 as 100% |
|---|---|
| SEQ ID 63 | 46% |
| SEQ ID 64 | 56% |
| SEQ ID 65 | 59% |
| SEQ ID 66 | 46% |
| SEQ ID 67 | 61% |
| SEQ ID 68 | 70% |
| SEQ ID 69 | 69% |
| SEQ ID 70 | 62% |
| SEQ ID 71 | 69% |
| SEQ ID 72 | 73% |
| SEQ ID 73 | 54% |
| SEQ ID 74 | 60% |
| SEQ ID 75 | 77% |
| SEQ ID 76 | 72% |
| SEQ ID 77 | 66% |
| SEQ ID 78 | 68% |

Example 8—Expression of Anti-PSMA/Anti-CD3 BiTE Antibody

This example shows the expression of the anti-PSMA/anti-CD3 bi-specific T-cell engager antibody. The signal peptide SEQ ID NO: 19 was cloned at the 5' end of a sequence encoding the mature anti-PSMA/anti-CD bi-specific T cell engager antibody in the construct of FIG. 10a.

The bi-specific Ab was expressed using the TEF promoter derived from the host organism.

The host strain was transformed with this constructs as a circular plasmid. 18 transformants were screened for integration of the cassette based on secretion of the engager antibody. The untransformed host (#267) and the anti-CD19/anti-CD3 bi-specific Ab fused to SEQ ID NO: 19 (from the previous example) were used as controls. Each clone was cultured overnight in 2.5 mL FM2 in a 24-well plate. They were then diluted 1000× into fresh FM2 (2.5 mL) and incubated for approximately 24 hours. The cells were pelleted by centrifugation (2000 g×5 min) and the supernatants assayed for the bi-specific Ab by Western analysis. Westerns were probed with an anti-His antibody and detected using an HRP-conjugated anti-mouse antibody and ECL-Plus. Chemifluorescence was detected using a Typhoon™ FLA 9000. The results are shown in FIG. 10b. Clones 1, 4, 5, 8, 9, 11, 12 and 17 secreted the anti-PSMA/anti-CD3 bi-specific Ab.

Example 9—Expression of an IgG2 Antibody Denosumab (Prolla®)

This example shows the expression of an IgG2 antibody. SEQ ID NO: 19 signal peptide was cloned at the 5' end of sequences encoding the mature heavy chain and light chain for the IgG2 antibody (denosumab). The heavy and light chains were expressed using the TEF promoter derived from the host organism. nptII and hph were used as selection markers.

Constructs were linearized and co-transformed into *Aurantiochytrium* sp. Transformants were screened for resistance to both paromomycin and hygromycin to identify clones carrying both constructs. Diagnostic PCR confirmed the presence of both light chain and heavy chain sequences. Six positive clones were examined for expression of denosumab. Each clone was cultured overnight in 2.5 mL FM2 in a 24-well plate. They were then diluted 1000× into fresh FM2 (2.5 mL) and incubated for approximately 24 hours. The cells were pelleted by centrifugation (2000 g×5 min) and the supernatants assayed for IgG2 using the Human IgG subclass profile kit. All clones produced the IgG2 antibody (Table 2).

TABLE 2

Titers of IgG2 Denosumab, from *Aurantiochytrium* sp.

| Clone # | Titers of IgG2 (mg/L) |
|---|---|
| 5 | 18 |
| 9 | 19 |
| 11 | 17 |
| 12 | 19 |
| 14 | 18 |
| 17 | 18 |

Example 10—Expression of the IgG4 Antibody Natalizumab (Tysabri®)

This example shows the expression of an IgG4 antibody. SEQ ID NO: 19 signal peptide was cloned at the 5' end of sequences encoding the mature heavy chain and light chain for the IgG4 antibody natalizumab. The heavy and light chains were expressed using the TEF promoter derived from the host organism. nptII and hph were used as selection markers.

Constructs were linearized and co-transformed into *Aurantiochytrium* sp. Transformants were screened for resistance to both paromomycin and hygromycin to identify clones carrying both constructs. Diagnostic PCR confirmed the presence of both light chain and heavy chain sequences. Five positive clones were examined for expression of natalizumab. Each clone was cultured overnight in 2.5 mL FM2 in a 24-well plate. They were then diluted 1000× into fresh FM2 (2.5 mL) and incubated for approximately 24 hours. The cells were pelleted by centrifugation (2000 g×5 min) and the supernatants assayed for IgG4 using the Human IgG subclass profile kit. All clones produced the IgG4 antibody (Table 3).

TABLE 3

Titers of the IgG4 natalizumab from *Aurantiochytrium* sp.

| Clone # | Titers of IgG2 (mg/L) |
|---|---|
| 3 | 44 |
| 14 | 54 |
| 15 | 49 |
| 20 | 30 |
| 31 | 95 |

Example 11—Expression of Kappa/Lambda Bi-Specific Antibody (Anti-Il6RC/Anti-IFNgamma This example shows the expression of a Kappa/Lambda bispecific antibody. The signal peptide SEQ ID NO: 19 was cloned at the 5' end of sequences encoding the mature heavy chain, kappa light chain and lambda light chain for the bispecific anti-Il6RC/anti-IFN antibody. The heavy and light chains were expressed using the TEF promoter derived from the host organism. nptII, hph and nat were used as selection markers.

Constructs were linearized and co-transformed into *Aurantiochytrium* sp. Transformants were screened for resistance to paromomycin, hygromycin and nourseothricin to identify clones carrying all three constructs. Diagnostic PCR confirmed the presence of the heavy chain and both light chain sequences. Nine positive clones were examined for expression of the bispecific anti-Il6RC/anti-IFNγ antibody. The untransformed *Aurantiochytrium* sp was used as negative control. Each clone was cultured overnight in 2.5 mL FM2 in a 24-well plate. They were then diluted 1000× into fresh FM2 (2.5 mL) and incubated for approximately 24 hours. The cells were pelleted by centrifugation (2000 g×5 min) and the supernatants assayed for the bispecific anti-Il6RC/anti-IFNγ antibody by Western analysis. Western blots were probed with an anti-human Ig antibody and detected using an HRP-conjugated anti-goat antibody and ECL-Plus. Chemifluorescence was detected using a Typhoon™ FLA 9000. All clones produced the heavy chain and the two light chains (FIG. 11).

Example 12—Expression of Hybrid Antibody XENP13551 (Anti-CD38/Anti-CD3

This example shows the expression of a hybrid antibody. The signal peptide SEQ ID NO: 19 was cloned at the 5' end of sequences encoding the mature heavy chain 1, heavy chain 2, and light chain for the hybrid bispecific anti-CD38/anti-CD3 antibody (XENP13551). The heavy and light chains were expressed using the TEF promoter derived from the host organism. nptII, hph and nat were used as selection markers.

Constructs were linearized and co-transformed into *Aurantiochytrium* sp. Transformants were screened for resistance to paromomycin, hygromycin and nourseothricin to identify clones carrying all three constructs. Diagnostic PCR confirmed the presence of the heavy chain and both light chain sequences. Nine positive clones were examined for expression of the hybrid bispecific anti-CD38/anti-CD3 antibody (XENP13551). The untransformed *Aurantiochytrium* sp (#267) was used as negative control. Each clone was cultured overnight in 2.5 mL FM2 in a 24-well plate. They were then diluted 1000× into fresh FM2 (2.5 mL) and incubated for approximately 24 hours. The cells were pelleted by centrifugation (2000 g×5 min) and the supernatants assayed for the hybrid bispecific anti-CD38/anti-CD3 antibody (XENP13551) by Western analysis. Western blots were probed with an anti-human Ig antibody and detected using an HRP-conjugated anti-goat antibody and ECL-Plus. Chemifluorescence was detected using a Typhoon™ FLA 9000. All clones produced heavy chain 1, heavy chain 2 and the light chain (FIG. 12).

Example 13—Expression of TagBFP-His6

This example shows the expression of TagBFP-His6 (TagBFP with a C-terminal 6× His-tag). The signal peptide SEQ ID NO: 19 was cloned at the 5' end of sequences encoding TagBFP. TagBFP was expressed using the TEF promoter derived from the host organism. hph was used as selection marker.

This construct was linearized and transformed into *Aurantiochytrium* sp. Transformants were screened for resistance to hygromycin to identify clones carrying TagBFP, which was confirmed by diagnostic PCR. Two positive clones were examined for expression of TagBFP. The untransformed *Aurantiochytrium* sp (#267) was used as negative control. Each clone was cultured overnight in 25 mL FM2 in a 250 mL baffled shake flask. The cells were pelleted by centrifugation (2000 g×5 min) and the supernatants assayed for TagBFP by fluorescence. 200 µL of the supernatant was placed in wells of a black round-bottom 96-well plate and fluorescence measure using a 96-well plate reader (top read, Ex=402 nm, Em=457 nm, Cutoff-=455 nm). The increase in relative fluorescence in the clones carrying the TagBFP indicates that this protein is being expressed and secreted (FIG. 13).

Example 14—Expression of K3-His6

This example shows the expression of K3-His6 (human plasminogen Kringle 3 domain with a C-terminal 6×His tag). The signal peptide SEQ ID NO: 19 was cloned at the 5' end of sequences encoding K3-His6. K3-His6 was expressed using the TEF promoter derived from the host organism. hph was used as selection marker.

This construct was linearized and transformed into *Aurantiochytrium* sp. Transformants were screened for resistance to hygromycin to identify clones carrying K3-His6, which was confirmed by diagnostic PCR. Three positive clones were examined for expression of K3-His6. The untransformed *Aurantiochytrium* sp (#267) was used as negative control. Each clone was cultured overnight in 2.5 mL FM2 in a 24-well plate. The cells were pelleted by centrifugation (2000 g×5 min) and the supernatants assayed for K3-His6. Westerns were probed with an anti-His antibody (HIS.H8) and detected using an HRP-conjugated anti-mouse antibody and ECL-Plus. Chemifluorescence was detected using a Typhoon™ FLA 9000. The results are shown in FIG. 14. All clones expressed and secreted K3-His6.

Although the invention has been described with reference to the above examples, it will be understood that modifications and variations are encompassed within the spirit and scope of the invention. Accordingly, the invention is limited only by the following claims.

The invention claimed is:

1. A recombinant Labyrinthulomycetes cell comprising an expression cassette that encodes a heterologous protein and a functional signal sequence that directs the secretion of the heterologous protein from the cell, wherein
   a. the signal sequence has at least 90% sequence identity to a sequence of at least 10 contiguous amino acids in the amino acid sequence selected from any one of SEQ ID NOs: 19, 72, 75, and 76;
   b. the signal sequence has at least 95% sequence identity to a sequence of at least 10 contiguous amino acids in the amino acid sequence of SEQ ID NO: 20, or the signal sequence has at least 90% sequence identity to a sequence of at least 15 contiguous amino acids in the amino acid sequence of SEQ ID NOs: 20, or the signal sequence has at least 90% sequence identity to a sequence of at least 20 contiguous amino acids in the amino acid sequence of SEQ ID NO: 20; or
   c. the signal sequence is encoded by a nucleic acid sequence having at least 90% sequence homology to any one of SEQ ID NOs: 31, 32, 88, 91, and 92.

2. The cell of claim 1 wherein the heterologous protein is a therapeutic protein.

3. The cell of claim 1 wherein the heterologous protein is a functional antibody.

4. The cell of claim 3 wherein the functional antibody comprises at least one heavy chain and at least one light chain.

5. The cell of claim 3 wherein the antibody is selected from the group consisting of: eculizumab, natalizumab, cetuximab, omalizumab, usteinumab, panitumumab, denosumab, trastuzumab and adalimumab.

6. The cell of claim 1 wherein the heterologous protein comprises a bispecific T cell engager.

7. The cell of claim 1 wherein the heterologous protein comprises a binding molecule that binds to an antigen selected from the group consisting of: anti-CD19, anti-CD3, anti-CD38, and prostate-specific membrane antigen (PSMA).

8. The cell of claim 1 wherein the expression cassette encodes a promoter active in a Labyrinthulomycetes and that regulates transcription of the heterologous protein.

9. The cell of claim 8 wherein the promoter is selected from the group consisting of: tubulinα promoter (tubαp) or translation elongation factor (TEFp) promoter.

10. The cell of claim 8 wherein the expression cassette further encodes a terminator selected from pgk1t or eno2t.

11. The cell of claim 3 wherein the antibody has at least 90% sequence identity to an amino acid sequence of at least 100 contiguous amino acids selected from the group consisting of SEQ ID NO: 5-8.

12. An *Aurantiochytrium* cell comprising an expression cassette that encodes a heterologous protein and a functional signal sequence that directs the secretion of the heterologous protein from the cell, wherein
   a. the signal sequence has at least 90% sequence identity to a sequence of at least 10 contiguous amino acids in the amino acid sequence selected from any one of SEQ ID NOs: 19, 72, 75, and 76;
   b. the signal sequence has at least 95% sequence identity to a sequence of at least 10 contiguous amino acids in the amino acid sequence of SEQ ID NO: 20, or the signal sequence has at least 90% sequence identity to a sequence of at least 15 contiguous amino acids in the amino acid sequence of SEQ ID NOs: 20, or the signal sequence has at least 90% sequence identity to a sequence of at least 20 contiguous amino acids in the amino acid sequence of SEQ ID NO: 20; or
   c. the signal sequence is encoded by a nucleic acid sequence having at least 90% sequence homology to any one of SEQ ID NOs: 31, 32, 88, 91, and 92.

13. The cell of claim 12 wherein the heterologous protein is a functional antibody.

14. The cell of claim 13 wherein the antibody has a light chain and a heavy chain.

15. The cell of claim 12 wherein
   the signal sequence has at least 90% sequence identity to at least 20 contiguous amino acids in the amino acid sequence selected from any one of SEQ ID NOs: 19, 20, 72, 75, and 76.

16. The cell of claim 12 wherein the signal sequence is encoded by a nucleotide sequence having at least 90% sequence identity to a nucleotide sequence of at least 120 contiguous nucleotides selected from any one of SEQ ID NOs: 31, 32, 88, 91, and 92.

17. A therapeutic protein comprising an antibody molecule linked to a signal sequence selected from the group consisting of SEQ ID NOs: 19, 20, 72, 75, and 76.

18. The therapeutic protein of claim 17 wherein the antibody is anti-TNF-alpha or anti-HER2.

19. The cell of claim 1, wherein:
a. the signal sequence is selected from any one of SEQ ID NOs: 19, 20, 72, 75, and 76; or
b. the signal sequence is encoded by the nucleic acid sequence selected from any one of SEQ ID NOs: 31, 32, 88, 91, and 92.

20. The cell of claim 12, wherein:
a. the signal sequence is selected from any one of SEQ ID NOs: 19, 20, 72, 75, and 76; or
b. the signal sequence is encoded by the nucleic acid sequence selected from any one of SEQ ID NOs: 31, 32, 88, 91, and 92.

21. The cell of claim 12 wherein the expression cassette further comprises a promoter active in *Aurantiochytrium* operably linked to the coding sequence of the heterologous protein, and a terminator sequence active in *Aurantiochytrium*.

\* \* \* \* \*

SEQUENCE LISTING

```
<160> NUMBER OF SEQ ID NOS: 94

<210> SEQ ID NO 1
<211> LENGTH: 645
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mature_anti-TNF-alpha_light_chain_nuc

<400> SEQUENCE: 1
gacatccaaa tgacacaaag cccttctagc cttagcgctt ctgttggtga tcgtgtgacc      60
attacatgtc gtgcttctca gggtattcgc aactatttag cctggtacca gcagaaacct     120
ggtaaagctc ctaagctcct catctatgct gcttctacac ttcaatctgg cgtgccttct     180
cgcttttctg gttctggttc tggtaccgat ttcacactca ccattagctc tcttcagcct     240
gaggatgttg ctacatacta ctgtcaacgc tacaacagag ccccttacac atttggtcaa     300
ggcacaaagg tggagattaa gcgtacagtt gctgctccta gcgtgttcat ttttcctcct     360
tctgatgagc agctcaagtc tggtacagct tctgttgttt gcctcctcaa caacttctac     420
cctagagaag ctaaggtgca gtggaaggtt gataacgctc ttcaatctgg caactctcag     480
gagtctgtta cagagcaaga cagcaaggat agcacctact ctctttctag caccccttacc      540
```

```
cttagcaagg ctgattacga gaagcacaag gtttacgctt gcgaggttac acatcagggt      600
ctttcttctc ctgtgaccaa gagctttaac cgtggtgaat gttaa                     645

<210> SEQ ID NO 2
<211> LENGTH: 1353
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mature_anti-TNF-alpha_heavy_chain_nuc

<400> SEQUENCE: 2
gaggttcagc ttgtagaaag tggtggtggt cttgttcaac tggtagatc tcttcgcctt       60 tcttgtgctg cttctggctt tacctttgac gattacgcta tgcactgggt tcgtcaagct     120
cctggtaaag gtttagagtg ggttagcgct attacctgga actctggcca cattgattac     180
gctgattctg ttgaaggccg cttcaccatt tctcgtgata tgctaagaa cagcctctac      240 ctccagatga actctcttag agctgaggat acagccgtgt actattgtgc taaggtgagc     300
tacctctcta ccgcttcttc tcttgattac tggggtcaag gcacacttgt gacagtttct     360
tctgcttcta ccaagggtcc tagcgttttt cctttagctc cttctagcaa gagcacatct     420
ggtggtacag ctgctttagg ttgccttgtt aaggactact ccctgaacc tgtgacagtt      480 tcttggaact ctggtgctct acatctggc gttcacacat tcctgctgt tcttcagtct       540 tctggcctct attctcttag ctctgtggtt acagtgcctt cttcttctct tggtacacag     600
acctacatct gcaacgttaa ccacaagcct agcaacacaa aggtggacaa gaaggttgag    660
cctaagtctt gcgataagac ccatacatgt cctccttgtc ctgctcctga attattaggt     720
ggtcctagcg tgttcctctt tcctcctaaa cctaaggaca ccctcatgat ttctcgcaca    780
cctgaagtta catgcgttgt ggttgacgtt tctcacgaag atcctgaggt gaagttcaac    840
tggtacgttg atggtgtgga ggttcataac gctaagacaa aacctcgtga ggagcagtac    900
cagtctacat atcgtgttgt gagcgtgctt accgttcttc atcaagattg gcttaacggc     960
aaggagtaca gtgcaaggt gtctaataag gctctccctg ctcctattga gaagaccatt    1020
tctaaggcta agggccaacc tagagagcct caagtttaca cacttcctcc ttctcgtgac   1080
gagcttacaa agaaccaggt gtctcttacc tgccttgtta gggcttttta ccctagcgac   1140
attgctgttg aatgggagtc taacggtcaa cctgagaaca actacaagac aacacctcct   1200
gtgcttgact ctgatggcag cttttttctc tacagcaagc ttaccgtgga caagtctaga   1260
tggcaacaag gtaacgtgtt ctcttgctct gtgatgcatg aggctcttca taaccactac   1320
acccagaagt ctcttagcct ttctcctggt taa                                1353

<210> SEQ ID NO 3
<211> LENGTH: 645
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mature_anti-HER2_light_chain_nuc

<400> SEQUENCE: 3
gacatccaaa tgacacaaag cccttctagc cttagcgctt ctgttggtga tcgtgtgacc      60
attacatgtc gtgcttctca ggatgtgaac acagctgttg cttggtacca acaaaagcct    120
```

```
ggtaaagctc ctaagctcct catttacagc gctagctttc tctactctgg cgttccttct      180
cgcttttctg gttctagatc tggcaccgat ttcacactca ccattagctc tcttcagcct      240
gaggattttg ccacatacta ctgccagcag cactacacaa cacctcctac atttggtcaa      300
ggcacaaagg tggagattaa gcgtacagtt gctgctccta gcgtgttcat ttttcctcct      360
tctgatgagc agctcaagtc tggtacagct tctgttgttt gcctcctcaa caacttctac      420
cctagagaag ctaaggtgca gtggaaggtt gataacgctc ttcaatctgg caactctcag      480
gagtctgtta cagagcaaga cagcaaggat agcacctact ctctttctag caccccttacc    540 cttagcaagg ctgattacga aagcacaag gtttacgctc gcgaggttac acatcagggt       600
ctttcttctc ctgtgaccaa gagctttaac cgtggtgaat gttaa                     645
```

<210> SEQ ID NO 4
<211> LENGTH: 1296
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mature_anti-HER2_heavy_chain_nuc

<400> SEQUENCE: 4

```
gaggttcagc ttgtagaaag tggtggtggt cttgttcaac tggtggttc tcttcgtctt       60 tcttgtgctg cttctggctt caacatcaag gatacctaca tccactgggt tcgtcaagct     120
cctggtaaag gttagagtg ggttgctcgc atttacccta caaatggcta cacacgttac      180
gctgatagcg ttaaaggccg ctttaccatt tctgctgata cctctaagaa caccgcctac     240
cttcagatga actctcttag agctgaggat acagccgtgt actattgttc tagatggggt     300
ggtgacggct tttatgctat ggattattgg ggtcagggca cacttgtgac agtttcttct     360
gcttctacca aggtcctag cgttttttcct ttagctcctt ctagcaagag cacatctggt     420
ggtacagctg ctttaggttg ccttgttaag gactacttcc ctgaacctgt gacagtttct     480
tggaactctg gtgctcttac atctggcgtt cacacatttc ctgctgttct tcagtcttct     540
ggcctctatt ctcttagctc tgtggttaca gtgccttctt cttctcttgg tacacagacc     600
tacatctgca acgttaacca caagcctagc aacacaaagg tggacaagaa ggttgagcct     660
aagtcttgcg ataagaccca tacatgtcct ccttgtcctg ctcctgaatt attaggtggt     720
cctagcgtgt tcctctttcc tcctaaacct aaggacaccc tcatgatttc tcgcacacct     780
gaagttacat gcgttgtggt tgacgtttct cacgaagatc ctgaggtgaa gttcaactgg     840
tacgttgatg gtgtggaggt tcataacgct aagacaaaac ctcgtgagga gcagtacaac     900
tctacatatc gcgtggttag cgtgcttaca gttcttcatc aggactggct aacggtaag      960 gagtataagt gcaaggtgag caacaaggct cttcctgctc ctattgagaa gaccattagc    1020
aaggctaagg gccaacctag agaacctcaa gtttacacac tccctccttc tcgtgaagag    1080
atgacaaaga accaggtgtc tcttacctgc cttgttaagg cttttaccc tagcgacatt     1140 gctgttgaat gggagtctaa cggtcaacct gagacaact acaagacaac acctcctgtg    1200
cttgactctg atggcagctt tttctctac agcaagctta ccgtggacaa gtctagatgg   1260
caacaaggta acgtgttctc ttgctctgtg atgcat                             1296
```

<210> SEQ ID NO 5
<211> LENGTH: 214

```
<212> TYPE: PRT
<213> ORGANISM: Homo sapiens
<220> FEATURE:
<221> NAME/KEY: misc_feature
<223> OTHER INFORMATION: mature_anti-TNF-alpha_light_chain_pept

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 6
<211> LENGTH: 450
<212> TYPE: PRT
<213> ORGANISM: Homo sapiens
<220> FEATURE:
<221> NAME/KEY: misc_feature
<223> OTHER INFORMATION: mature_anti-TNF-alpha_heavy_chain_pept

<400> SEQUENCE: 6

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Val Ser Tyr Leu Ser Thr Ala Ser Ser Leu Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Gln Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly
    450

<210> SEQ ID NO 7
<211> LENGTH: 214
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mature_anti-HER2_light_chain_pept
```

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 449
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: mature_anti-HER2_heavy_chain_pept

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

-continued

```
Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly
```

<210> SEQ ID NO 9
<211> LENGTH: 35
<212> TYPE: PRT
<213> ORGANISM: Schizochytrium sp.
<220> FEATURE:
<221> NAME/KEY: misc_feature
<223> OTHER INFORMATION: #548, Schizo Pi-IIIb2, encoded by Seq 21

<400> SEQUENCE: 9

```
Met Ala Asn Ile Met Ala Asn Val Thr Pro Gln Gly Val Ala Lys Gly
1               5                   10                  15
```

```
Phe Gly Leu Phe Val Gly Val Leu Phe Leu Tyr Trp Phe Leu Val
            20                  25                  30

Gly Leu Ala
        35

<210> SEQ ID NO 10
<211> LENGTH: 30
<212> TYPE: PRT
<213> ORGANISM: Schizochytrium sp.
<220> FEATURE:
<221> NAME/KEY: misc_feature
<223> OTHER INFORMATION: #549, SEC1, encoded by Seq 22

<400> SEQUENCE: 10

Met Lys Phe Ala Thr Ser Val Ala Ile Leu Leu Val Ala Asn Ile Ala
1               5                   10                  15

Thr Ala Leu Ala Gln Ser Asp Gly Cys Thr Pro Thr Asp Gln
            20                  25                  30

<210> SEQ ID NO 11
<211> LENGTH: 30
<212> TYPE: PRT
<213> ORGANISM: Schizochytrium sp.
<220> FEATURE:
<221> NAME/KEY: misc_feature
<223> OTHER INFORMATION: #552, i1485, encoded by Seq 23

<400> SEQUENCE: 11

Met Lys Phe Ala Thr Ser Val Ala Ile Val Leu Val Ala Asn Val Ala
1               5                   10                  15

Thr Ala Leu Ala Gln Ser Asp Gly Cys Thr Ala Thr Asp Gln
            20                  25                  30

<210> SEQ ID NO 12
<211> LENGTH: 17
<212> TYPE: PRT
<213> ORGANISM: Gaussia princeps
<220> FEATURE:
<221> NAME/KEY: misc_feature
<223> OTHER INFORMATION: # 556, from gLUC, encoded by Seq 24

<400> SEQUENCE: 12

Met Gly Val Lys Val Leu Phe Ala Leu Ile Cys Ile Ala Val Ala Glu
1               5                   10                  15

Ala

<210> SEQ ID NO 13
<211> LENGTH: 21
<212> TYPE: PRT
<213> ORGANISM: Homo sapiens
<220> FEATURE:
<221> NAME/KEY: misc_feature
<223> OTHER INFORMATION: #557, Ig kappa, encoded by Seq 25

<400> SEQUENCE: 13

Met Glu Thr Asp Thr Leu Leu Leu Trp Val Leu Leu Leu Trp Val Pro
1               5                   10                  15

Gly Ser Thr Gly Asp
            20

<210> SEQ ID NO 14
<211> LENGTH: 30
<212> TYPE: PRT
<213> ORGANISM: Homo sapiens
<220> FEATURE:
```

```
<221> NAME/KEY: misc_feature
<223> OTHER INFORMATION: #558, from Ig gamma1, encoded by Seq 26

<400> SEQUENCE: 14

Met Asp Trp Thr Trp Arg Phe Leu Phe Val Val Ala Ala Val Thr Gly
1               5                   10                  15

Val Gln Ser Gln Val Gln Leu Val Gln Ser Gly Ala Glu Val
            20                  25                  30

<210> SEQ ID NO 15
<211> LENGTH: 20
<212> TYPE: PRT
<213> ORGANISM: Batrachochytrium dendrobatidis
<220> FEATURE:
<221> NAME/KEY: misc_feature
<223> OTHER INFORMATION: #575, signal sequence, encoded by Seq 27

<400> SEQUENCE: 15

Met Lys Ile Phe Gln Phe Val Ile Ala Gly Leu Ala Ala Leu Ser Leu
1               5                   10                  15

Val Ser Ala Gly
            20

<210> SEQ ID NO 16
<211> LENGTH: 22
<212> TYPE: PRT
<213> ORGANISM: Batrachochytrium dendrobatidis
<220> FEATURE:
<221> NAME/KEY: misc_feature
<223> OTHER INFORMATION: #576, encoded by Seq 28

<400> SEQUENCE: 16

Met Met Lys Ser Val Ala Thr Leu Gly Cys Leu Leu Ala Phe Leu Ala
1               5                   10                  15

His Thr Val Ser Ala Gly
            20

<210> SEQ ID NO 17
<211> LENGTH: 16
<212> TYPE: PRT
<213> ORGANISM: Spizellomyces sp.
<220> FEATURE:
<221> NAME/KEY: misc_feature
<223> OTHER INFORMATION: #577, encoded by Seq 29

<400> SEQUENCE: 17

Met Lys Ala Ser Ala Thr Leu Leu Leu Ala Leu Ala Ala Thr Thr Ala
1               5                   10                  15

<210> SEQ ID NO 18
<211> LENGTH: 19
<212> TYPE: PRT
<213> ORGANISM: Batrachochytrium dendrobatidis
<220> FEATURE:
<221> NAME/KEY: misc_feature
<223> OTHER INFORMATION: #578, encoded by Seq 30

<400> SEQUENCE: 18

Met Leu Pro Lys Ile Leu Thr Ile Val Val Ala Val Phe Ala Gly Leu
1               5                   10                  15

Val Ala Ala

<210> SEQ ID NO 19
<211> LENGTH: 27
<212> TYPE: PRT
```

<213> ORGANISM: Batrachochytrium dendrobatidis
<220> FEATURE:
<221> NAME/KEY: misc_feature
<223> OTHER INFORMATION: #579, encoded by Seq 31

<400> SEQUENCE: 19

Met Pro Phe Asn Arg Leu Ser Leu Pro Cys Leu Leu Leu Ala Leu Ile
1               5                   10                  15

Ala Ser Leu Phe Ile His Ala Ala Gln Ala Gly
            20                  25

<210> SEQ ID NO 20
<211> LENGTH: 27
<212> TYPE: PRT
<213> ORGANISM: Aurantiochytrium sp.
<220> FEATURE:
<221> NAME/KEY: misc_feature
<223> OTHER INFORMATION: from KAR2, encoded by Seq 32

<400> SEQUENCE: 20

Met Ala Gly Met Lys Thr Lys Phe Ala Gln Ala Val Val Leu Leu Ala
1               5                   10                  15

Ala Phe Leu Ala Val Ile Gly Gly Val Arg Ala
            20                  25

<210> SEQ ID NO 21
<211> LENGTH: 105
<212> TYPE: DNA
<213> ORGANISM: Schizochytrium sp.
<220> FEATURE:
<221> NAME/KEY: misc_feature
<223> OTHER INFORMATION: #548, Schizo Pi-IIIb2, encodes Seq 9

<400> SEQUENCE: 21
atggccaaca tcatggcaaa cgtgacacct caaggcgttg ctaagggttt tggccttttt      60
gttggcgtgc tcttcttcct ttactggttt cttgtgggcc ttgct                     105

<210> SEQ ID NO 22
<211> LENGTH: 90
<212> TYPE: DNA
<213> ORGANISM: Schizochytrium sp.
<220> FEATURE:
<221> NAME/KEY: misc_feature
<223> OTHER INFORMATION: #549, SEC1, encodes Seq 10

<400> SEQUENCE: 22
atgaagttcg ctacctctgt cgccattctc cttgttgcta acatcgctac cgctcttgct      60
cagtctgatg gttgtacacc taccgatcaa                                       90

<210> SEQ ID NO 23
<211> LENGTH: 90
<212> TYPE: DNA
<213> ORGANISM: Schizochytrium sp.
<220> FEATURE:
<221> NAME/KEY: misc_feature
<223> OTHER INFORMATION: #552, encodes Seq 11

<400> SEQUENCE: 23
atgaagttcg ctacctctgt cgccattgtg cttgttgcta acgttgctac cgctcttgct      60
cagtctgatg gttgtacagc taccgatcaa                                       90

<210> SEQ ID NO 24
<211> LENGTH: 51
<212> TYPE: DNA

```
<213> ORGANISM: Gaussia princeps
<220> FEATURE:
<221> NAME/KEY: misc_feature
<223> OTHER INFORMATION: #556, encodes Seq 12

<400> SEQUENCE: 24
atgggcgtta aggtactgtt tgcactcatc tgcatcgctg ttgctgaagc t         51

<210> SEQ ID NO 25
<211> LENGTH: 63
<212> TYPE: DNA
<213> ORGANISM: Homo sapiens
<220> FEATURE:
<221> NAME/KEY: misc_feature
<223> OTHER INFORMATION: #557, encodes Seq 13

<400> SEQUENCE: 25
atggagaccg ataccctttt gctctgggtg cttcttcttt gggttcctgg ttctacaggc   60
gat                                                                63

<210> SEQ ID NO 26
<211> LENGTH: 90
<212> TYPE: DNA
<213> ORGANISM: Homo sapiens
<220> FEATURE:
<221> NAME/KEY: misc_feature
<223> OTHER INFORMATION: #558, encodes Seq 14

<400> SEQUENCE: 26
atggattgga catggcgctt tctctttgtg gttgctgctg ttacaggcgt tcagtctcag   60
gttcagcttg ttcaatctgg tgctgaggtt                                    90

<210> SEQ ID NO 27
<211> LENGTH: 60
<212> TYPE: DNA
<213> ORGANISM: Batrachochytrium dendrobatidis
<220> FEATURE:
<221> NAME/KEY: misc_feature
<223> OTHER INFORMATION: chyPDI, encodes Seq 15

<400> SEQUENCE: 27
atgaagatct tccagttcgt tatcgctggc ttagctgctc tttctcttgt ttctgctggc   60

<210> SEQ ID NO 28
<211> LENGTH: 66
<212> TYPE: DNA
<213> ORGANISM: Batrachochytrium dendrobatidis
<220> FEATURE:
<221> NAME/KEY: misc_feature
<223> OTHER INFORMATION: #576, encodes Seq 16, XP006675927

<400> SEQUENCE: 28
atgatgaagt ctgtggccac tcttggttgc cttcttgctt ttcttgctca cacagtgtct   60
gctggt                                                              66

<210> SEQ ID NO 29
<211> LENGTH: 48
<212> TYPE: DNA
<213> ORGANISM: Spizellomyces sp.
<220> FEATURE:
<221> NAME/KEY: misc_feature
<223> OTHER INFORMATION: #577, KNC97388, encodes Seq 17

<400> SEQUENCE: 29
atgaaggcat cagcaacact cctccttgct ttagctgcta caactgct               48
```

<210> SEQ ID NO 30
<211> LENGTH: 57
<212> TYPE: DNA
<213> ORGANISM: Batrachochytrium dendrobatidis
<220> FEATURE:
<221> NAME/KEY: misc_feature
<223> OTHER INFORMATION: #578, XP006681835, encodes Seq 18

<400> SEQUENCE: 30
atgctcccta agattctcac cattgttgtg gctgtgtttg ctggtcttgt tgctgct            57

<210> SEQ ID NO 31
<211> LENGTH: 81
<212> TYPE: DNA
<213> ORGANISM: Batrachochytrium dendrobatidis
<220> FEATURE:
<221> NAME/KEY: misc_feature
<223> OTHER INFORMATION: #579, XP006680331, encodes Seq 19

<400> SEQUENCE: 31
atgcccttta accgcctttc tcttccttgc cttcttcttg ctctcattgc tagcctcttc            60
attcatgctg ctcaagctgg t                                                     81

<210> SEQ ID NO 32
<211> LENGTH: 81
<212> TYPE: DNA
<213> ORGANISM: Aurantiochytrium sp.
<220> FEATURE:
<221> NAME/KEY: misc_feature
<223> OTHER INFORMATION: KAR2, encodes Seq 20

<400> SEQUENCE: 32
atggcaggta tgaagaccaa attcgcccag gccgttgtgc ttctggccgc ttttttggct            60
gtcattggcg gtgtacgcgc t                                                     81

<210> SEQ ID NO 33
<211> LENGTH: 29
<212> TYPE: PRT
<213> ORGANISM: Aurantiochytrium sp.
<220> FEATURE:
<221> NAME/KEY: misc_feature
<223> OTHER INFORMATION: encoded by Seq 48, conserved predicted protein

<400> SEQUENCE: 33

Met Ala Arg Ala Trp Ala Ser Ser Val Ala Ala Arg Ala Leu Ala Thr
1               5                   10                  15

Leu Cys Leu Leu Ala Val Leu Ala Thr Ile Ala Glu Ala
            20                  25

<210> SEQ ID NO 34
<211> LENGTH: 26
<212> TYPE: PRT
<213> ORGANISM: Aurantiochytrium sp.
<220> FEATURE:
<221> NAME/KEY: misc_feature
<223> OTHER INFORMATION: protein disulfide isomerase A4, encoded by Seq
      49

<400> SEQUENCE: 34

Met Asn Lys Phe Val His Leu Leu Ile Ala Ala Leu Ala Val Ile Ala
1               5                   10                  15

Thr Asn Leu Leu Ser Val Asn Ala Glu Ala
            20                  25

```
<210> SEQ ID NO 35
<211> LENGTH: 27
<212> TYPE: PRT
<213> ORGANISM: Aurantiochytrium sp.
<220> FEATURE:
<221> NAME/KEY: misc_feature
<223> OTHER INFORMATION: Luminal-binding protein 5 (KAR2), encoded by
      Seq 50

<400> SEQUENCE: 35

Met Ala Gly Met Lys Thr Lys Phe Ala Gln Ala Val Val Leu Leu Ala
1               5                   10                  15

Ala Phe Leu Ala Val Ile Gly Gly Val Arg Ala
            20                  25

<210> SEQ ID NO 36
<211> LENGTH: 30
<212> TYPE: PRT
<213> ORGANISM: Aurantiochytrium sp.
<220> FEATURE:
<221> NAME/KEY: misc_feature
<223> OTHER INFORMATION: Mesencephalic astrocyte-derived neurotrophic
      factor-like protein, encoded by Seq 51

<400> SEQUENCE: 36

Met Ser Ala Gly Phe Ser Arg Arg Ala Met Leu Ala Trp Val Leu Met
1               5                   10                  15

Leu Val Ala Ala Phe Ala Ser Leu Ala Val Ser Val Glu Ala
            20                  25                  30

<210> SEQ ID NO 37
<211> LENGTH: 22
<212> TYPE: PRT
<213> ORGANISM: Aurantiochytrium sp.
<220> FEATURE:
<221> NAME/KEY: misc_feature
<223> OTHER INFORMATION: Heat shock 70 kDa protein 17, encoded by Seq 52

<400> SEQUENCE: 37

Met Asn Trp Lys Thr Ser Trp Leu Val Val Leu Val Ala Ala Ala Val
1               5                   10                  15

Ala Ile Ala Ala Asp Ala
            20

<210> SEQ ID NO 38
<211> LENGTH: 46
<212> TYPE: PRT
<213> ORGANISM: Aurantiochytrium sp.
<220> FEATURE:
<221> NAME/KEY: misc_feature
<223> OTHER INFORMATION: GDH/6PGL endoplasmic bifunctional protein,
      encoded by Seq 53

<400> SEQUENCE: 38

Met Thr Ser Gly Ala Tyr Tyr Lys Ser Arg Gln Ser Thr Leu Pro Trp
1               5                   10                  15

Leu Ile Asn Gly Ser Arg Met Ser His Val Leu Arg Ala Ile Leu Val
            20                  25                  30

Ala Leu Val Val Val Gly Leu Leu Leu Pro Ser Thr Ala Gly
        35                  40                  45

<210> SEQ ID NO 39
<211> LENGTH: 39
<212> TYPE: PRT
<213> ORGANISM: Aurantiochytrium sp.
```

```
<220> FEATURE:
<221> NAME/KEY: misc_feature
<223> OTHER INFORMATION: alpha/beta-hydrolases, encoded by Seq 54

<400> SEQUENCE: 39

Met Leu Ser Ser Val Thr Arg Leu Ser Arg Ser Pro Phe Ser Leu Arg
1               5                   10                  15

Leu Pro Arg Ser Leu Arg Leu Leu Gly Val Gly Leu Thr Met Ala Asn
            20                  25                  30

Leu Phe Gly Ser Val Ala Ala
        35

<210> SEQ ID NO 40
<211> LENGTH: 25
<212> TYPE: PRT
<213> ORGANISM: Aurantiochytrium sp.
<220> FEATURE:
<221> NAME/KEY: misc_feature
<223> OTHER INFORMATION: from Ankyrin repeat domain-containing protein
      55 isoform 1, encoded by Seq 55

<400> SEQUENCE: 40

Met Val Ala His Ser Gln Arg Lys Trp Phe Phe Gly Leu Leu Phe Thr
1               5                   10                  15

Ser Leu Gln Ala Leu Leu Gly Tyr Ser
            20                  25

<210> SEQ ID NO 41
<211> LENGTH: 25
<212> TYPE: PRT
<213> ORGANISM: Aurantiochytrium sp.
<220> FEATURE:
<221> NAME/KEY: misc_feature
<223> OTHER INFORMATION: from Ankyrin repeat domain-containing protein
      56 isoform 1, encoded by Seq 56

<400> SEQUENCE: 41

Met Val Ala His Ser Gln Arg Lys Trp Phe Phe Gly Leu Leu Phe Thr
1               5                   10                  15

Ser Leu Gln Ala Leu Leu Gly His Ser
            20                  25

<210> SEQ ID NO 42
<211> LENGTH: 22
<212> TYPE: PRT
<213> ORGANISM: Aurantiochytrium sp.
<220> FEATURE:
<221> NAME/KEY: misc_feature
<223> OTHER INFORMATION: from chaperone protein DNAJ, encoded by Seq 57

<400> SEQUENCE: 42

Met Arg Ala Ser Ala Trp Cys Arg Lys Leu Ser Val Val Leu Ile Leu
1               5                   10                  15

Val Tyr Leu Val Val Ser
            20

<210> SEQ ID NO 43
<211> LENGTH: 30
<212> TYPE: PRT
<213> ORGANISM: Aurantiochytrium sp.
<220> FEATURE:
<221> NAME/KEY: misc_feature
<223> OTHER INFORMATION: Conserved predicted protein, encoded by Seq 58

<400> SEQUENCE: 43
```

```
Met Gly Leu Thr Arg Arg Gly Ala Tyr Ser Ser Val Ala Ala Leu Ala
1               5                   10                  15

Val Val Leu Cys Leu Leu Ile Phe Leu Asn Pro Ser Ser Ala
            20                  25                  30
```

<210> SEQ ID NO 44
<211> LENGTH: 39
<212> TYPE: PRT
<213> ORGANISM: Aurantiochytrium sp.
<220> FEATURE:
<221> NAME/KEY: misc_feature
<223> OTHER INFORMATION: Predicted protein, encoded by Seq 59

<400> SEQUENCE: 44

```
Met Met Asn Trp Ser Ile Pro Ser Thr Ser Ala Trp Lys Thr Ser Val
1               5                   10                  15

Phe Val Arg Thr Lys Thr Ala Ala Ile Leu Ala Ile Cys Ile Leu Ser
            20                  25                  30

Ser Leu Ala Thr Ala Asn Ser
        35
```

<210> SEQ ID NO 45
<211> LENGTH: 30
<212> TYPE: PRT
<213> ORGANISM: Aurantiochytrium sp.
<220> FEATURE:
<221> NAME/KEY: misc_feature
<223> OTHER INFORMATION: Mesencephalic astrocyte-derived neurotrophic
      factor-like protein, encoded by Seq 60

<400> SEQUENCE: 45

```
Met Ser Ser Gly Phe Ser Arg Arg Ala Met Leu Ala Trp Val Leu Met
1               5                   10                  15

Leu Val Ala Ala Phe Ala Ser Leu Ala Val Ser Val Glu Ala
            20                  25                  30
```

<210> SEQ ID NO 46
<211> LENGTH: 34
<212> TYPE: PRT
<213> ORGANISM: Aurantiochytrium sp.
<220> FEATURE:
<221> NAME/KEY: misc_feature
<223> OTHER INFORMATION: Conserved predicted protein, encoded by Seq 61

<400> SEQUENCE: 46

```
Met Ser Met Gly Leu Thr Arg Arg Gly Ala Tyr Ser Ser Val Ala Ala
1               5                   10                  15

Leu Ala Val Leu Leu Cys Leu Leu Ile Ser Leu Asn Pro Ser Ser Ala
            20                  25                  30

Arg Ala
```

<210> SEQ ID NO 47
<211> LENGTH: 33
<212> TYPE: PRT
<213> ORGANISM: Aurantiochytrium sp.
<220> FEATURE:
<221> NAME/KEY: misc_feature
<223> OTHER INFORMATION: Conserved predicted protein, encoded by Seq 62

<400> SEQUENCE: 47

```
Met Ser Val Met Gly Leu Thr Arg Arg Gly Ala Tyr Ser Ser Val Ala
1               5                   10                  15

Ala Leu Ala Val Val Leu Cys Leu Leu Ile Phe Leu Asn Pro Ser Ser
            20                  25                  30
```

Ala

<210> SEQ ID NO 48
<211> LENGTH: 87
<212> TYPE: DNA
<213> ORGANISM: Aurantiochytrium sp.
<220> FEATURE:
<221> NAME/KEY: misc_feature
<223> OTHER INFORMATION: conserved predicted protein, encodes Seq 33

<400> SEQUENCE: 48
atggctcgcg catgggcttc tagtgtggct gctcgggcat tagcgacact ctgcctctta    60
gctgtccttg ccactattgc ggaagca                                        87

<210> SEQ ID NO 49
<211> LENGTH: 78
<212> TYPE: DNA
<213> ORGANISM: Aurantiochytrium sp.
<220> FEATURE:
<221> NAME/KEY: misc_feature
<223> OTHER INFORMATION: from protein disulfide-isomerase A4, encodes
      Seq 34

<400> SEQUENCE: 49
atgaacaagt tcgtccacct tttaattgca gcacttgctg ttatcgcgac taacttgctt    60
tctgttaatg ctgaagct                                                  78

<210> SEQ ID NO 50
<211> LENGTH: 81
<212> TYPE: DNA
<213> ORGANISM: Aurantiochytrium sp.
<220> FEATURE:
<221> NAME/KEY: misc_feature
<223> OTHER INFORMATION: Luminal-binding protein S (KAR2), encodes Seq
      35

<400> SEQUENCE: 50
atggcaggta tgaagaccaa attcgcccag gccgttgtgc ttctggccgc ttttttggct    60
gtcattggcg gtgtacgcgc c                                              81

<210> SEQ ID NO 51
<211> LENGTH: 90
<212> TYPE: DNA
<213> ORGANISM: Aurantiochytrium sp.
<220> FEATURE:
<221> NAME/KEY: misc_feature
<223> OTHER INFORMATION: Mesencephalic astrocyte-derived neurotrophic
      factor-like protein, encodes Seq 36

<400> SEQUENCE: 51
atgtcggcag gattttctcg acgcgccatg ttggcgtggg tgctcatgct tgtagcagcc    60
tttgcatcgc tcgccgtttc ggtggaggca                                     90

<210> SEQ ID NO 52
<211> LENGTH: 66
<212> TYPE: DNA
<213> ORGANISM: Aurantiochytrium sp.
<220> FEATURE:
<221> NAME/KEY: misc_feature
<223> OTHER INFORMATION: from heat shock 70 kDa protein 17, encodes Seq
      37

<400> SEQUENCE: 52
atgaactgga aaacttcatg gctcgtcgtc ctcgtggcgg cggccgtcgc tattgctgca    60

```
gatgca                                                              66

<210> SEQ ID NO 53
<211> LENGTH: 138
<212> TYPE: DNA
<213> ORGANISM: Aurantiochytrium sp.
<220> FEATURE:
<221> NAME/KEY: misc_feature
<223> OTHER INFORMATION: from GDH/6PGL endoplasmic bifunctional protein,
      encodes Seq 38

<400> SEQUENCE: 53
atgacatccg gtgcttacta caaatcccgg cagagtactt tgccatggct cataaatgga    60
tcacgtatga gtcatgtgtt gagagctatt ctggtcgctt tagttgttgt aggtcttttg   120
ctgccgagca ctgccgga                                                138

<210> SEQ ID NO 54
<211> LENGTH: 117
<212> TYPE: DNA
<213> ORGANISM: Aurantiochytrium sp.
<220> FEATURE:
<221> NAME/KEY: misc_feature
<223> OTHER INFORMATION: alpha/beta- hydrolase, encodes Seq 39

<400> SEQUENCE: 54
atgctttctt cggttactag actttctcgc agccccttt cgctgcgtct gccccggtct     60
cttcgtcttt tgggcgtagg tctgacaatg gctaaccttt tggttccgt cgctgct       117

<210> SEQ ID NO 55
<211> LENGTH: 75
<212> TYPE: DNA
<213> ORGANISM: Aurantiochytrium sp.
<220> FEATURE:
<221> NAME/KEY: misc_feature
<223> OTHER INFORMATION: Ankyrin repeat domain-containing protein 54,
      isoform 1, encodes Seq 40

<400> SEQUENCE: 55
atggtagcac actctcaaag gaaatggttc tttggtcttc ttttcacatc tttacaagct    60
ttgctcggat attca                                                    75

<210> SEQ ID NO 56
<211> LENGTH: 75
<212> TYPE: DNA
<213> ORGANISM: Aurantiochytrium sp.
<220> FEATURE:
<221> NAME/KEY: misc_feature
<223> OTHER INFORMATION: Ankyrin repeat domain-containing protein 54,
      isoform 1, encodes Seq 41

<400> SEQUENCE: 56
atggtagcac actctcaaag gaaatggttc tttggtcttc ttttcacatc tttacaagct    60
ttgctcggac attca                                                    75

<210> SEQ ID NO 57
<211> LENGTH: 66
<212> TYPE: DNA
<213> ORGANISM: Aurantiochytrium sp.
<220> FEATURE:
<221> NAME/KEY: misc_feature
<223> OTHER INFORMATION: from chaperone protein DNAJ, encodes Seq 42

<400> SEQUENCE: 57
```

```
atgagggctt cggcatggtg ccgaaagctt agtgttgtgc tcattcttgt gtacctggta    60
gtctcg                                                              66
```

<210> SEQ ID NO 58
<211> LENGTH: 90
<212> TYPE: DNA
<213> ORGANISM: Aurantiochytrium sp.
<220> FEATURE:
<221> NAME/KEY: misc_feature
<223> OTHER INFORMATION: Conserved predicted protein, encodes Seq 43,
      from various organisms

<400> SEQUENCE: 58

```
atgggactca cccgtcgcgg tgcatattcc agcgtggcgg cactcgcggt agtcctgtgt    60
cttctgattt ttcttaatcc ttcttctgcg                                    90
```

<210> SEQ ID NO 59
<211> LENGTH: 117
<212> TYPE: DNA
<213> ORGANISM: Aurantiochytrium sp.
<220> FEATURE:
<221> NAME/KEY: misc_feature
<223> OTHER INFORMATION: Predicted protein, encodes Seq 44

<400> SEQUENCE: 59

```
atgatgaact ggagcatacc gagcacttct gcgtggaaga catctgtgtt tgtaagaaca    60
aagactgcag ctattttggc catatgtatc ctgagtagcc tcgcgactgc aaatagt     117
```

<210> SEQ ID NO 60
<211> LENGTH: 90
<212> TYPE: DNA
<213> ORGANISM: Aurantiochytrium sp.
<220> FEATURE:
<221> NAME/KEY: misc_feature
<223> OTHER INFORMATION: from mesencephalic astrocyte-derived
      neurotrophic factor-like protein, encodes Seq 45

<400> SEQUENCE: 60

```
atgtcgtcag gattttctcg acgcgccatg ttggcgtggg tgctcatgct tgtagcagcc    60
tttgcatcgc tcgccgtttc ggtggaggca                                    90
```

<210> SEQ ID NO 61
<211> LENGTH: 102
<212> TYPE: DNA
<213> ORGANISM: Aurantiochytrium sp.
<220> FEATURE:
<221> NAME/KEY: misc_feature
<223> OTHER INFORMATION: Conserved predicted protein, encodes Seq 46,
      from various organisms

<400> SEQUENCE: 61

```
atgagcatgg gactcacccg tcgcggtgca tattccagcg tggcggcact cgcggtactc    60
ctgtgtcttc tgatttctct taatccttct tctgcgcgtg ca                     102
```

<210> SEQ ID NO 62
<211> LENGTH: 99
<212> TYPE: DNA
<213> ORGANISM: Aurantiochytrium sp.
<220> FEATURE:
<221> NAME/KEY: misc_feature
<223> OTHER INFORMATION: Conserved predicted protein, encodes Seq 47

<400> SEQUENCE: 62

```
atgagcgtca tgggactcac ccgtcgcggt gcatattcca gcgtggcggc actcgcggta    60
```

```
gtcctgtgtc ttctgatttt tcttaatcct tcttctgcg                        99
```

<210> SEQ ID NO 63
<211> LENGTH: 18
<212> TYPE: PRT
<213> ORGANISM: Aurantiochytrium sp.
<220> FEATURE:
<221> NAME/KEY: misc_feature
<223> OTHER INFORMATION: #601, signal peptide, encoded by Seq 79

<400> SEQUENCE: 63

Met Gln Ala Phe Thr Ala Ile Val Met Leu Ala Leu Ala Gly Val Ser
1               5                   10                  15

Ser Ala

<210> SEQ ID NO 64
<211> LENGTH: 19
<212> TYPE: PRT
<213> ORGANISM: Aurantiochytrium sp.
<220> FEATURE:
<221> NAME/KEY: misc_feature
<223> OTHER INFORMATION: #602, signal peptide, encoded by Seq 80

<400> SEQUENCE: 64

Met Lys Phe Glu Ser Val Ile Ala Leu Leu Ile Leu Ala Val Thr Ser
1               5                   10                  15

Ser Glu Ala

<210> SEQ ID NO 65
<211> LENGTH: 19
<212> TYPE: PRT
<213> ORGANISM: Aurantiochytrium sp.
<220> FEATURE:
<221> NAME/KEY: misc_feature
<223> OTHER INFORMATION: #603, signal peptide, encoded by Seq 81

<400> SEQUENCE: 65

Met Pro Pro Phe Ala Phe Leu Ala Ile Ala Phe Ala Leu Leu Gly Phe
1               5                   10                  15

Ala Lys Ala

<210> SEQ ID NO 66
<211> LENGTH: 19
<212> TYPE: PRT
<213> ORGANISM: Aurantiochytrium sp.
<220> FEATURE:
<221> NAME/KEY: misc_feature
<223> OTHER INFORMATION: #604, signal peptide, encoded by Seq 82

<400> SEQUENCE: 66

Met Gln Leu Ser Phe Ile Ala Leu Met Val Ala Ser Leu Ala Ser Met
1               5                   10                  15

Val Met Gly

<210> SEQ ID NO 67
<211> LENGTH: 20
<212> TYPE: PRT
<213> ORGANISM: Aurantiochytrium sp.
<220> FEATURE:
<221> NAME/KEY: misc_feature
<223> OTHER INFORMATION: #605, signal peptide, encoded by Seq 83

<400> SEQUENCE: 67

Met Ile Arg Ala Ser Val Ile Phe Val Ile Leu Ala Leu Ala Phe Ser

Ala Val Ser Ala
        20

<210> SEQ ID NO 68
<211> LENGTH: 20
<212> TYPE: PRT
<213> ORGANISM: Aurantiochytrium sp.
<220> FEATURE:
<221> NAME/KEY: misc_feature
<223> OTHER INFORMATION: #606, signal peptide, encoded by Seq 84

<400> SEQUENCE: 68

Met Met Lys Ala Ile Ala Leu Cys Met Val Leu Ala Leu Cys Asn Val
1               5                   10                  15

Leu Ala Ser Ala
        20

<210> SEQ ID NO 69
<211> LENGTH: 21
<212> TYPE: PRT
<213> ORGANISM: Aurantiochytrium sp.
<220> FEATURE:
<221> NAME/KEY: misc_feature
<223> OTHER INFORMATION: #607, signal peptide, encoded by Seq 85

<400> SEQUENCE: 69

Met Gly Ile Ser Pro Tyr Gly Leu Leu Ile Val Val Ala Leu Cys Leu
1               5                   10                  15

Asn Gln Val Thr Ala
        20

<210> SEQ ID NO 70
<211> LENGTH: 21
<212> TYPE: PRT
<213> ORGANISM: Aurantiochytrium sp.
<220> FEATURE:
<221> NAME/KEY: misc_feature
<223> OTHER INFORMATION: #608, signal peptide, encoded by Seq 86

<400> SEQUENCE: 70

Met Gly Ile Ser Pro Tyr Gly Leu Leu Ile Val Val Ala Leu Cys Leu
1               5                   10                  15

Asn Gln Val Thr Ala
        20

<210> SEQ ID NO 71
<211> LENGTH: 23
<212> TYPE: PRT
<213> ORGANISM: Aurantiochytrium sp.
<220> FEATURE:
<221> NAME/KEY: misc_feature
<223> OTHER INFORMATION: #609, signal peptide, encoded by Seq 87

<400> SEQUENCE: 71

Met Ile Gln Arg Gly Ala Thr Ile Leu Leu Val Leu Ser Ala Ile Leu
1               5                   10                  15

Ala Ser Ser Pro Val Tyr Ala
        20

<210> SEQ ID NO 72
<211> LENGTH: 23
<212> TYPE: PRT
<213> ORGANISM: Aurantiochytrium sp.
<220> FEATURE:

```
<221> NAME/KEY: misc_feature
<223> OTHER INFORMATION: #610, signal peptide, encoded by Seq 88

<400> SEQUENCE: 72

Met Asn Leu His Gly Leu Lys Ala Thr Cys Leu Ile Leu Ala Leu Ser
1               5                   10                  15
Met Leu Ala Thr Val His Gly
            20

<210> SEQ ID NO 73
<211> LENGTH: 25
<212> TYPE: PRT
<213> ORGANISM: Aurantiochytrium sp.
<220> FEATURE:
<221> NAME/KEY: misc_feature
<223> OTHER INFORMATION: #611, signal peptide, encoded by Seq 89

<400> SEQUENCE: 73

Met Thr Ala Leu Phe Lys Ser Leu Leu Leu Ala Leu Cys Cys Ala Phe
1               5                   10                  15
Val Ala Leu Pro Ser Pro Ala Ser Ala
            20                  25

<210> SEQ ID NO 74
<211> LENGTH: 26
<212> TYPE: PRT
<213> ORGANISM: Aurantiochytrium sp.
<220> FEATURE:
<221> NAME/KEY: misc_feature
<223> OTHER INFORMATION: #612, signal peptide, encoded by Seq 90

<400> SEQUENCE: 74

Met Thr Ser Ala Val Ala Thr Phe Thr Met Ala Ala Leu Leu Val Ile
1               5                   10                  15
Ala Phe Leu Gln Met Ser Ala Val Glu Ala
            20                  25

<210> SEQ ID NO 75
<211> LENGTH: 20
<212> TYPE: PRT
<213> ORGANISM: Aurantiochytrium sp.
<220> FEATURE:
<221> NAME/KEY: misc_feature
<223> OTHER INFORMATION: #613, signal peptide, encoded by Seq 91

<400> SEQUENCE: 75

Met Arg Val Leu Ala Phe Ile Ala Ala Cys Ile Leu Ala Ser Leu Glu
1               5                   10                  15
Ala Ser Cys Ala
            20

<210> SEQ ID NO 76
<211> LENGTH: 22
<212> TYPE: PRT
<213> ORGANISM: Aurantiochytrium sp.
<220> FEATURE:
<221> NAME/KEY: misc_feature
<223> OTHER INFORMATION: #614, signal peptide, encoded by Seq 92

<400> SEQUENCE: 76

Met Ala Thr Ser Ile Leu Val Thr Val Val Met Val Phe Ala Ile Leu
1               5                   10                  15
Ile Ala Ser Val Gln Ala
            20
```

<210> SEQ ID NO 77
<211> LENGTH: 26
<212> TYPE: PRT
<213> ORGANISM: Aurantiochytrium sp.
<220> FEATURE:
<221> NAME/KEY: misc_feature
<223> OTHER INFORMATION: #615, signal peptide, encoded by Seq 93

<400> SEQUENCE: 77

Met Gln Ile Ala Val Asn Lys Val Thr Leu Leu Leu Met Leu Leu Met
1               5                   10                  15

Ala Ser Thr Ser Leu Asp Ala Ala Arg Gly
            20                  25

<210> SEQ ID NO 78
<211> LENGTH: 46
<212> TYPE: PRT
<213> ORGANISM: Aurantiochytrium sp.
<220> FEATURE:
<221> NAME/KEY: misc_feature
<223> OTHER INFORMATION: #616, signal peptide, encoded by Seq 94

<400> SEQUENCE: 78

Met Thr Ser Gly Ala Tyr Tyr Lys Ser Arg Gln Ser Thr Leu Pro Trp
1               5                   10                  15

Leu Ile Asn Gly Ser Arg Met Ser His Val Leu Arg Ala Ile Leu Val
            20                  25                  30

Ala Leu Val Val Val Gly Leu Leu Leu Pro Ser Thr Ala Gly
            35                  40                  45

<210> SEQ ID NO 79
<211> LENGTH: 54
<212> TYPE: DNA
<213> ORGANISM: Aurantiochytrium sp.
<220> FEATURE:
<221> NAME/KEY: misc_feature
<223> OTHER INFORMATION: #601, signal peptide, encodes Seq 63

<400> SEQUENCE: 79
atgcaggctt tcaccgctat tgtcatgctt gcccttgcgg gtgtctcctc tgct        54

<210> SEQ ID NO 80
<211> LENGTH: 57
<212> TYPE: DNA
<213> ORGANISM: Aurantiochytrium sp.
<220> FEATURE:
<221> NAME/KEY: misc_feature
<223> OTHER INFORMATION: #602, signal peptide, encodes Seq 64

<400> SEQUENCE: 80
atgaagtttg aatctgtaat tgcgctgctc atcctggcgg taacttcaag cgaagct     57

<210> SEQ ID NO 81
<211> LENGTH: 57
<212> TYPE: DNA
<213> ORGANISM: Aurantiochytrium sp.
<220> FEATURE:
<221> NAME/KEY: misc_feature
<223> OTHER INFORMATION: #603, signal peptide, encodes Seq 65

<400> SEQUENCE: 81 atgccccct tcgccttcct tgcgattgcc tttgctcttc ttggctttgc caaagct      57

<210> SEQ ID NO 82
<211> LENGTH: 57

```
<212> TYPE: DNA
<213> ORGANISM: Aurantiochytrium sp.
<220> FEATURE:
<221> NAME/KEY: misc_feature
<223> OTHER INFORMATION: #604, signal peptide, encodes Seq 66

<400> SEQUENCE: 82
atgcagctct cttttattgc cctcatggtg gcctctttgg cctccatggt gatgggc      57

<210> SEQ ID NO 83
<211> LENGTH: 60
<212> TYPE: DNA
<213> ORGANISM: Aurantiochytrium sp.
<220> FEATURE:
<221> NAME/KEY: misc_feature
<223> OTHER INFORMATION: #605, signal peptide, encodes Seq 67

<400> SEQUENCE: 83
atgatccgtg ctagtgttat cttcgtcatc ctggcgctcg ccttctcggc tgtgtcggcc   60

<210> SEQ ID NO 84
<211> LENGTH: 60
<212> TYPE: DNA
<213> ORGANISM: Aurantiochytrium sp.
<220> FEATURE:
<221> NAME/KEY: misc_feature
<223> OTHER INFORMATION: #606, signal peptide, encodes Seq 68

<400> SEQUENCE: 84
atgatgaagg caattgctct gtgcatggtg cttgcactct gcaatgttct tgcttctgca   60

<210> SEQ ID NO 85
<211> LENGTH: 60
<212> TYPE: DNA
<213> ORGANISM: Aurantiochytrium sp.
<220> FEATURE:
<221> NAME/KEY: misc_feature
<223> OTHER INFORMATION: #607, signal peptide, encodes Seq 69

<400> SEQUENCE: 85
atgcggagcc tttcttttct cgtggcagtt gctgccactc ttattgcttc ggctcaggcc   60

<210> SEQ ID NO 86
<211> LENGTH: 63
<212> TYPE: DNA
<213> ORGANISM: Aurantiochytrium sp.
<220> FEATURE:
<221> NAME/KEY: misc_feature
<223> OTHER INFORMATION: #608, signal peptide, encodes Seq 70

<400> SEQUENCE: 86
atgggcattt ctccatacgg tttgctcatt gtagtggctc tctgcctaaa ccaagttact   60
gca                                                                 63

<210> SEQ ID NO 87
<211> LENGTH: 69
<212> TYPE: DNA
<213> ORGANISM: Aurantiochytrium sp.
<220> FEATURE:
<221> NAME/KEY: misc_feature
<223> OTHER INFORMATION: #609, signal peptide, encodes Seq 71

<400> SEQUENCE: 87
atgattcagc gtggagccac catccttctg gtgctcagtg cgatacttgc aagcagcccg   60
gtgtatgct                                                           69
```

<210> SEQ ID NO 88
<211> LENGTH: 69
<212> TYPE: DNA
<213> ORGANISM: Aurantiochytrium sp.
<220> FEATURE:
<221> NAME/KEY: misc_feature
<223> OTHER INFORMATION: #610, signal peptide, encodes Seq 72

<400> SEQUENCE: 88
atgaacctcc atggtttgaa ggctacatgt cttatcctgg ctttatcaat gcttgcgact    60
gtacacggg                                                            69

<210> SEQ ID NO 89
<211> LENGTH: 75
<212> TYPE: DNA
<213> ORGANISM: Aurantiochytrium sp.
<220> FEATURE:
<221> NAME/KEY: misc_feature
<223> OTHER INFORMATION: #611, signal peptide, encodes Seq 73

<400> SEQUENCE: 89
atgacggcac ttttcaagtc cttgcttttg gctctctgct gtgcctttgt ggcgctgccg    60
agccctgctt ccgca                                                     75

<210> SEQ ID NO 90
<211> LENGTH: 78
<212> TYPE: DNA
<213> ORGANISM: Aurantiochytrium sp.
<220> FEATURE:
<221> NAME/KEY: misc_feature
<223> OTHER INFORMATION: #612, signal peptide, encodes Seq 74

<400> SEQUENCE: 90
atgacctctg ctgtggcgac cttcaccatg gcagctctgc tcgtcattgc ttttctgcaa    60
atgtcagctg ttgaggca                                                  78

<210> SEQ ID NO 91
<211> LENGTH: 60
<212> TYPE: DNA
<213> ORGANISM: Aurantiochytrium sp.
<220> FEATURE:
<221> NAME/KEY: misc_feature
<223> OTHER INFORMATION: #613, signal peptide, encodes Seq 75

<400> SEQUENCE: 91
atgcgggttc ttgcttttat agctgcatgc attttagcct ctctcgaggc ttcatgtgca    60

<210> SEQ ID NO 92
<211> LENGTH: 66
<212> TYPE: DNA
<213> ORGANISM: Aurantiochytrium sp.
<220> FEATURE:
<221> NAME/KEY: misc_feature
<223> OTHER INFORMATION: #614, signal peptide, encodes Seq 76

<400> SEQUENCE: 92
atggcaactt caatccttgt caccgtggtg atggtgttcg ccatacttat cgcgtctgtg    60
caagct                                                               66

<210> SEQ ID NO 93
<211> LENGTH: 78
<212> TYPE: DNA
<213> ORGANISM: Aurantiochytrium sp.
<220> FEATURE:

```
<221> NAME/KEY: misc_feature
<223> OTHER INFORMATION: #615, signal peptide, encodes Seq 77

<400> SEQUENCE: 93
atgcaaatcg cagtgaataa agtaacccett cttttgatgc tgctcatggc tagcactagc    60
cttgatgcag ctcgtgga                                                   78

<210> SEQ ID NO 94
<211> LENGTH: 138
<212> TYPE: DNA
<213> ORGANISM: Aurantiochytrium sp.
<220> FEATURE:
<221> NAME/KEY: misc_feature
<223> OTHER INFORMATION: #616, signal peptide, encodes Seq 78

<400> SEQUENCE: 94
atgacatccg gtgcttacta caaatcccgg cagagtactt tgccatggct cataaatgga    60
tcacgtatga gtcatgtgtt gagagctatt ctggtcgctt tagttgttgt aggtcttttg   120
ctgccgagca ctgccgga                                                 138
```